US006794991B2

(12) United States Patent
Dungan

(10) Patent No.: US 6,794,991 B2
(45) Date of Patent: Sep. 21, 2004

(54) MONITORING METHOD

(75) Inventor: Cornelius P. Dungan, Shaker Heights, OH (US)

(73) Assignee: Gastronics' Inc., Cleveland, OH (US)

( * ) Notice: Subject to any disclaimer, the term of this patent is extended or adjusted under 35 U.S.C. 154(b) by 323 days.

(21) Appl. No.: 10/062,320

(22) Filed: Jan. 31, 2002

(65) Prior Publication Data

US 2002/0070869 A1 Jun. 13, 2002

Related U.S. Application Data

(63) Continuation-in-part of application No. 09/854,748, filed on May 14, 2001, now Pat. No. 6,670,887, which is a continuation-in-part of application No. 09/333,352, filed on Jun. 15, 1999, now Pat. No. 6,252,510.

(51) Int. Cl.$^7$ .............................................. G08B 17/10
(52) U.S. Cl. ............ 340/632; 340/539.19; 340/539.22; 340/693.5
(58) Field of Search ............................ 340/632, 539.17, 340/539.19, 539.22, 539.26, 539.3, 693.5

(56) References Cited

U.S. PATENT DOCUMENTS

| | | | | |
|---|---|---|---|---|
| 4,476,706 A | * | 10/1984 | Hadden et al. ............... 73/1.07 |
| 4,562,723 A | * | 1/1986 | Hubner ....................... 73/31.07 |
| 4,668,940 A | * | 5/1987 | Beard et al. ................. 340/521 |
| 5,132,968 A | | 7/1992 | Cephus ....................... 370/349 |
| 5,406,265 A | | 4/1995 | Trozzo et al. ................ 340/632 |
| 5,446,445 A | | 8/1995 | Bloomfield et al. .......... 340/521 |
| 5,481,181 A | | 1/1996 | McHardy et al. .......... 205/794.5 |
| 5,553,094 A | | 9/1996 | Johnson et al. ............. 375/130 |
| 5,568,121 A | | 10/1996 | Lamensdorf ........... 340/539.17 |
| 5,597,534 A | | 1/1997 | Kaiser ..................... 422/82.02 |
| 5,771,004 A | | 6/1998 | Suppelsa et al. ............ 340/632 |
| 5,822,373 A | | 10/1998 | Addy ......................... 375/259 |
| 5,861,316 A | | 1/1999 | Cage et al. .................... 436/52 |
| 5,898,369 A | | 4/1999 | Godwin ................. 340/539.26 |
| 6,114,964 A | | 9/2000 | Fasano ........................ 340/632 |
| 6,259,373 B1 | * | 7/2001 | Ghahramani ............. 340/815.4 |
| 6,369,715 B2 | * | 4/2002 | Bennett et al. ............. 340/618 |
| 6,415,646 B1 | * | 7/2002 | Kessel et al. ................ 73/23.2 |
| 6,490,530 B1 | * | 12/2002 | Wyatt .......................... 702/24 |

OTHER PUBLICATIONS

Gas Detection Systems Inc., publication entitled "Turn–Key Wireless Gas Detection", published prior to Oct. 14, 1998.
Gas Detection Systems, Inc. publication entitled "Stackpac", published prior to Oct. 14, 1998.
Gas Detection Systems, Inc. publication entitled "GDS–2000 Teledetection System", published prior to Oct. 14, 1998.
B&W Technologies Ltd. publication entitled "Wireless Multi–point Gas Monitoring–Rig Rat", published prior to Oct. 14, 1998.
Photographs (2) of Georgia Gulf Corporation installation in Louisiana prior to Oct. 14, 1998. Printing designating various components of the installation has been added to the photographs.

* cited by examiner

Primary Examiner—Daniel J. Wu
Assistant Examiner—Sihong Huang
(74) Attorney, Agent, or Firm—Tarolli, Sundheim, Covell & Tummino L.L.P.

(57) ABSTRACT

A monitoring system includes a master station and a plurality of monitor stations which are spaced from the master station. Each of the monitor stations includes a programmable computer which is connected with a radio and a sensor. The computer and radio may be enclosed in an explosion-proof housing. To change a program in the computer at a monitor station, the program change may be transmitted from the master station to the monitor station. In addition, data relating to a condition to be sensed may be transmitted from the master station to the monitor station.

114 Claims, 7 Drawing Sheets

MONITORING METHOD

RELATED APPLICATIONS

This application is a continuation-in-part of U.S. patent application Ser. No. 09/854,748 filed May 14, 2001 now U.S. Pat. No. 6,670,887. The aforementioned application Ser. No. 09/854,748 is itself a continuation-in-part of U.S. patent application Ser. No. 09/333,352 filed Jun. 15, 1999 (now U.S. Pat. No. 6,252,510). The benefit of the earlier filing dates of these applications is hereby claimed.

BACKGROUND OF THE INVENTION

The present invention relates to a method of monitoring for selected operating conditions.

Monitoring Systems have been provided to monitor many different types of conditions, such as, the presence of a toxic or flammable gas, wind speed and/or direction, fluid flow, heat, pressure, and force. The data stored at a known monitor stations may be changed by carrying a data entry device, such as a laptop computer, to the monitor stations. However, monitor stations may be located at a substantial distance or be relatively inaccessible. This may make the changing of data in known monitor stations relatively difficult. It may also be difficult to change a program in a computer or similar device in remote monitor stations.

The monitor stations may be used in an environment which may, under certain circumstances, contain ignitable concentrations of a flammable gas. In such a situation, it is important that the monitor station be constructed in such a manner as to prevent ignition of any flammable gases around the monitor station.

Portable monitor stations may be positioned in any desired location. However, it may be desired to have data indicative of the position of each monitor station available at a master station.

SUMMARY OF THE INVENTION

The present invention relates to a new and improved method and apparatus for monitoring for one or more selected conditions. The selected conditions may be the presence and/or concentration of a selected gas, wind speed and/or direction, the rate of fluid flow, temperature, pressure, and/or force. Of course, the apparatus could be utilized to sense for other conditions, or combinations of conditions, if desired.

A plurality of monitor stations may be provided at spaced apart locations. A programmable computer may be connected with a radio and a sensor at each of the monitor stations. During use of the apparatus, a computer program change may be transmitted from a master station radio to the radio in at least one of the monitor stations. In addition, or alternatively, data may be transmitted from the radio at the master station to the radios at each of the monitor stations. The data transmitted to the monitor stations may be utilized in computers at the monitor stations.

The computer and radio at each of the monitor stations may be enclosed in an explosion-proof housing which is sealed against the entry of gas from the atmosphere around the monitor station. Whether or not the housing is sealed against entry of gas, the housing may have a relatively large main opening which is closed with a relatively large main cover and a relatively small secondary opening which is closed with a relatively small secondary cover. Data relating to gas or other selected operating condition to be monitored may be entered into the computer by opening the relatively small secondary cover while the relatively large main cover remains closed.

Portable monitor stations may be provided. A global positioning system receiver may be provided at each of the portable monitor stations. The global positioning system receivers enable computers in the portable monitor stations to inform a master station of the locations of the portable monitor stations.

BRIEF DESCRIPTION OF THE DRAWINGS

The foregoing and other features of the present invention will become more apparent upon a consideration of the following description taken in connection with the accompanying drawings wherein.

DESCRIPTION OF SPECIFIC PREFERRED EMBODIMENTS

General Description

Figure 1:
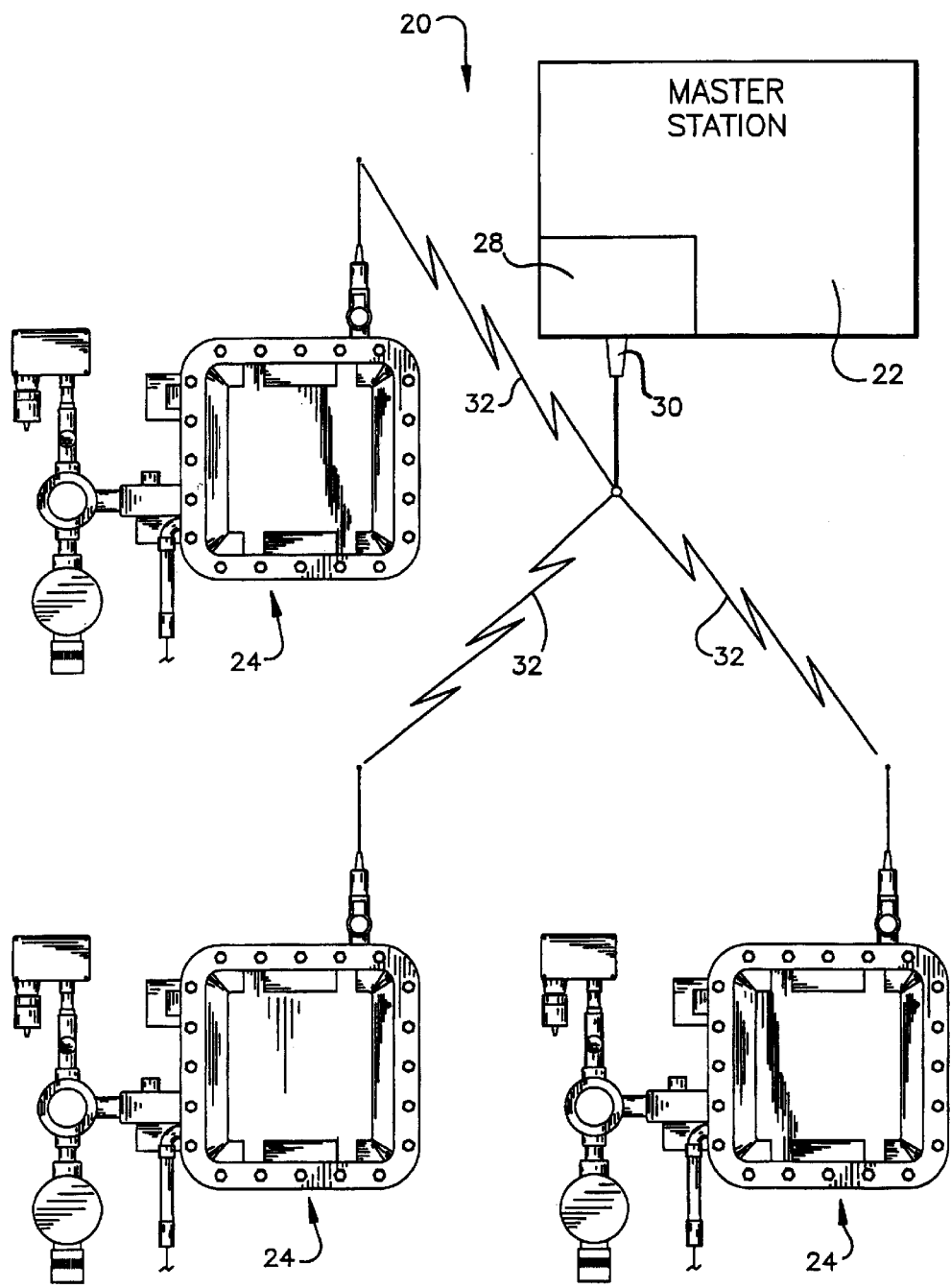
FIG. 1 is a schematic illustration depicting the relationship between a master station and a plurality of monitor stations.

A monitor system 20 is illustrated schematically in FIG. 1. The monitor system 20 includes a master station 22 and a plurality of monitor stations 24. A radio 28 at the master station 22 has an antenna 30. The radio 28 at the master station 22 is effective to transmit radio signals, indicated schematically at 32 in FIG. 1, to each of the monitor stations 24. The radio 28 at the master station 22 is also effective to receive radio signals from each of the monitor stations 24.

Figure 3:
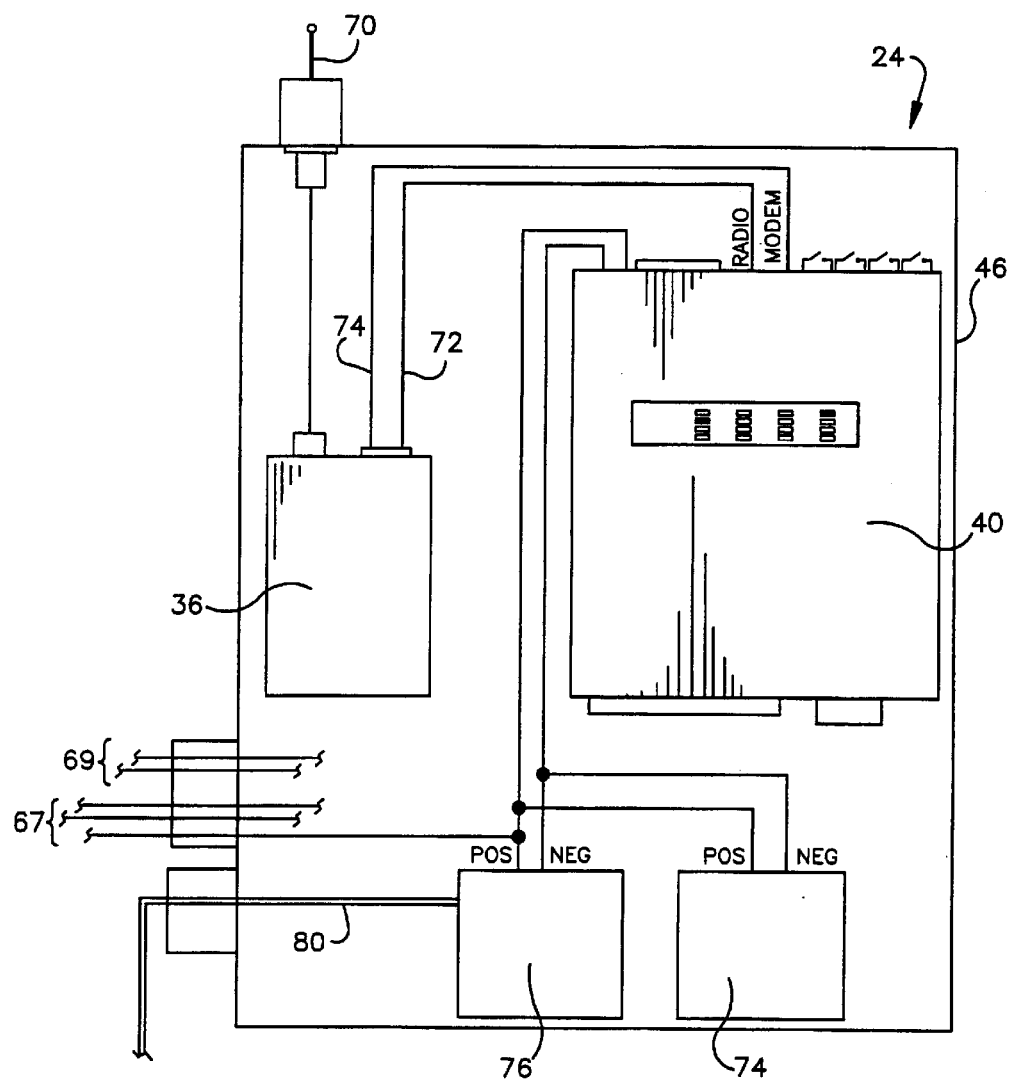
FIG. 3 is a schematic illustration depicting the relationship between a radio, computer, battery charger and battery in a housing at one of the monitor stations.

Similarly, the monitor stations 24 contain radios 36 (FIG. 3). The radios 36 at the monitor stations 24 are operable to transmit radio signals to the radio 28 at the master station 22. The radios 36 at the monitor stations 24 are effective to receive signals from the master station 22. The radios 28 and 36 in the master station 22 (FIG. 1) and monitor stations 24 (FIG. 3) enable data to be transmitted from the master station to the monitor stations and enable data to be transmitted from the monitor stations to the master station.

In accordance with one of the features of the present invention, the radio 28 in the master station 22 (FIG. 1) may be operated to transmit data relating to a condition to be sensed to the radio 36 in the monitor station 24. The data is conducted from the radio 36 to the computer 40 at the monitor station 24. The data is stored in the monitor station computer 40.

In accordance with another feature of the present invention, the radio 28 in the master station 22 may be utilized to transmit a computer program change from the master station 22 to the radio 36 in a monitor station 24 (FIG. 3). The program in the computer 40 is changed in accordance with the computer program change transmitted from the radio 28 in the master station 22 to the radio 36 in the monitor stations 24.

Figure 10:
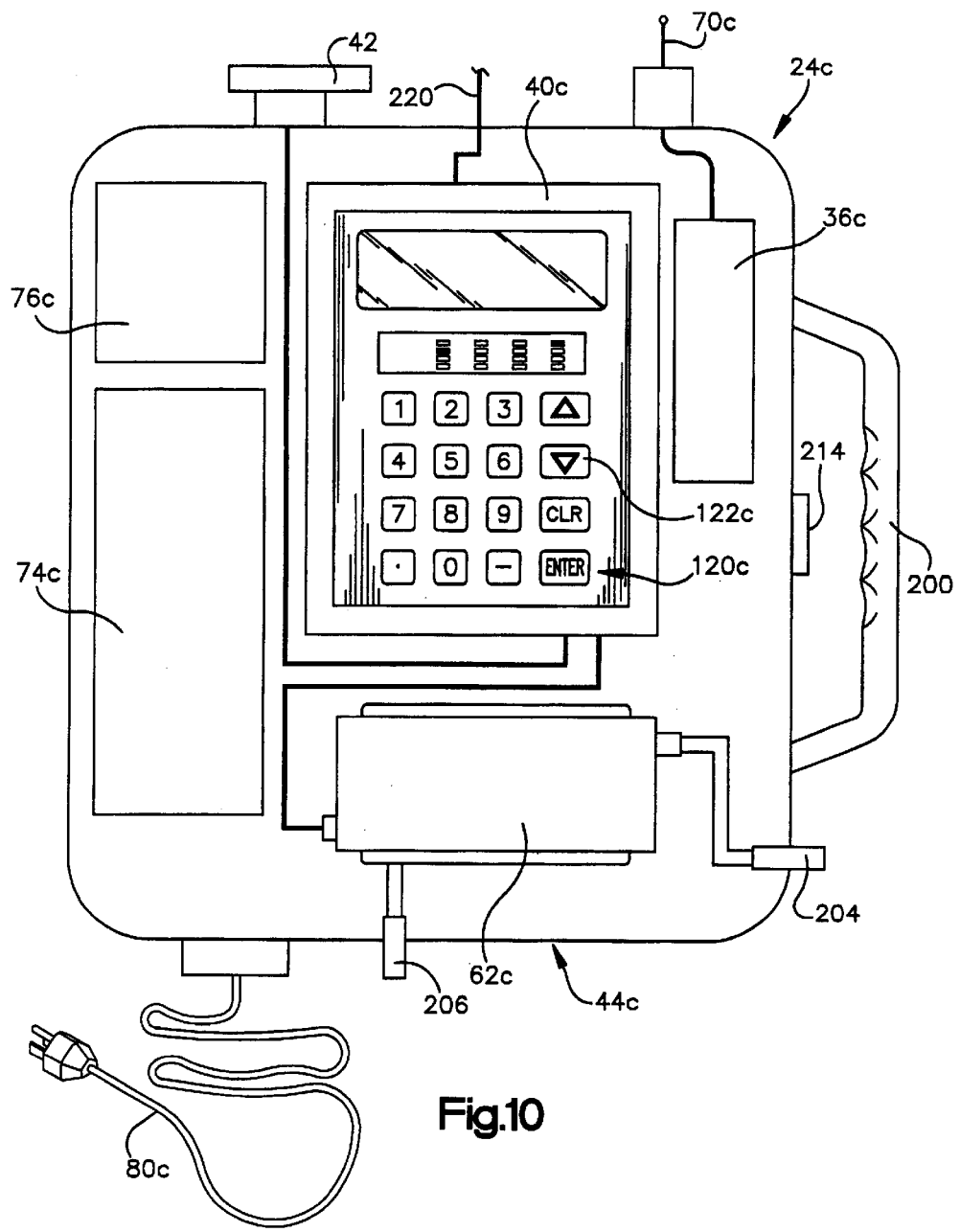
FIG. 10 is a schematic illustration of a portable monitor station.

In accordance with another feature of the invention, the monitor stations 24 may be portable. The portable monitor stations 24 may be provided with global positioning system receiver 42 (FIG. 10). The global positioning system receiver 42 enables the radios 36 in the monitor stations 24 to transmit the locations of the monitor stations to the master station 22.

Figure 2:
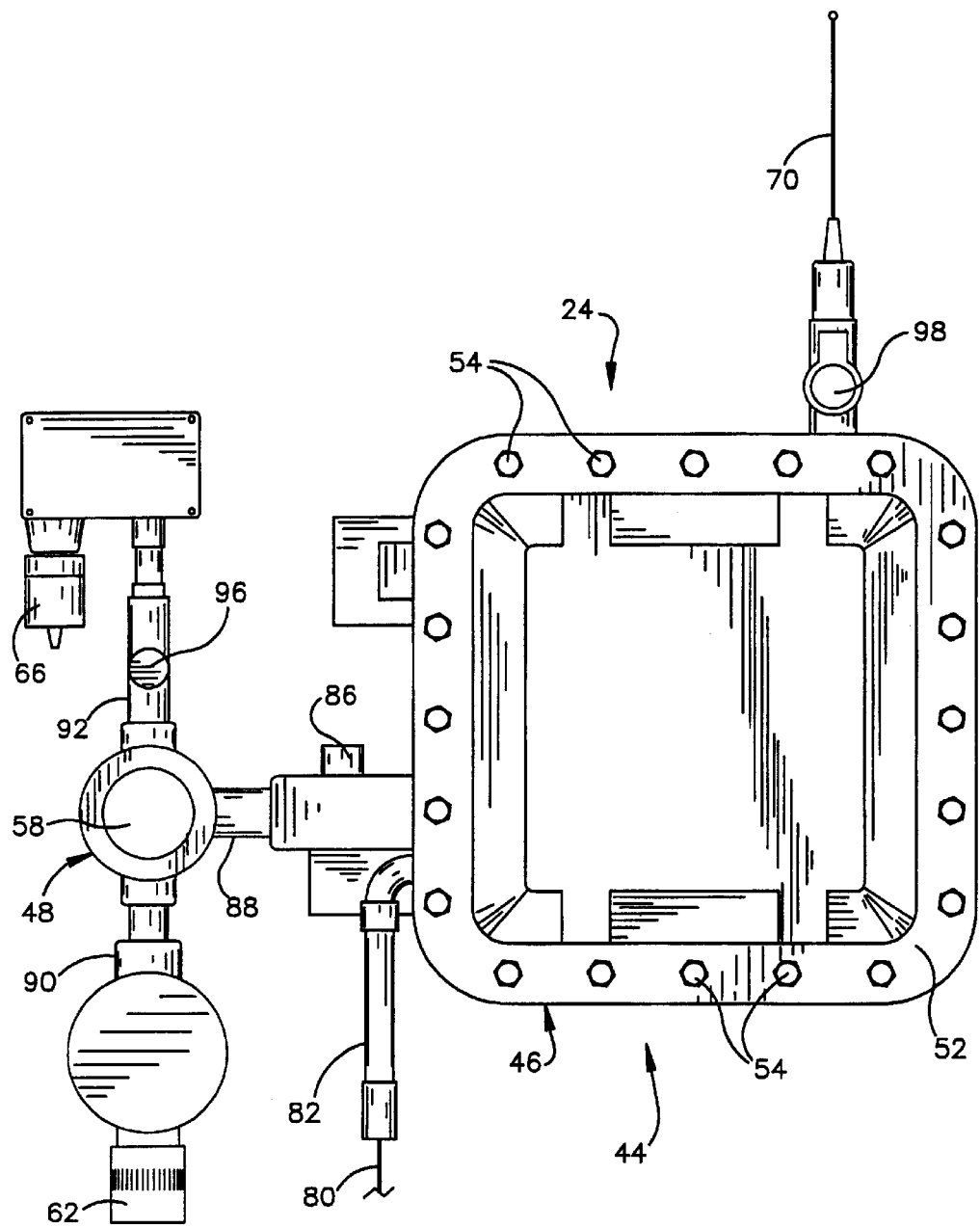
FIG. 2 is an enlarged illustration of one of the monitor stations of FIG. 1.

In accordance with another feature of the invention, the monitor stations 24 may have explosion-proof housings 44 (FIG. 2). The explosion-proof housing 44 enables the monitor stations 24 to be located in environments which may contain ignitable concentrations of flammable gases, vapors, combustible dust, and/or liquids. The explosion-proof housing 44 is capable of withstanding, without damage, an explosion which may occur within the housing. The explosion-proof housing 44 is also capable of preventing ignition of ignitable concentrations of flammable gases, vapors, combustible dust, and/or liquid in an environment surrounding the enclosure as a result of a spark and/or explosion within the housing.

Explosion-Proof Housing

The explosion-proof housing 44 (FIG. 2) may include an explosion-proof main housing 46 and an explosion-proof secondary housing 48. If desired, rather than including a plurality of housings, that is, the main housing 46 and secondary housing 48, the gas monitor station 24 could have a single explosion-proof housing. Alternatively, three or more housings could be interconnected to form the explosion-proof housing 44.

The illustrated explosion-proof main housing 46 includes a relatively large main cover 52 which is secured to a rectangular, generally box-shaped, base by bolts or other suitable fasteners 54. It should be understood that the main housing 46 could have configuration other than the illustrated rectangular configuration. It should also be understood that the main cover 52 could be connected with the main housing 46 in a manner other than by the fasteners 54. For example, the main housing 46 could have a circular configuration with a cover which is connected with a base container by one or more hinges and/or one or more latches.

The cover 52 and base of the main housing 48 are cast, copper-free aluminum. However, it should be understood that the cover 52 and base of the main housing could be cast of other materials, if desired.

The explosion-proof secondary housing 48 has a generally cylindrical configuration and includes a relatively small cover 58 of cast copper-free aluminum having a threaded connection (not shown) with a cylindrical base. The base of the secondary housing 48 is also formed of cast copper-free aluminum. The small cover 58 may be removed from the base of the secondary housing 48 by merely spinning the cover in a counterclockwise direction (as viewed in FIG. 2). Similarly, the cover 58 may be installed on the base of the secondary housing 48 by merely spinning the cover in a clockwise direction.

It should be understood that the secondary housing 48 could have a configuration other than the illustrated cylindrical configuration and that the cover 58 could be connected with the base in a manner other than with a threaded interconnection. For example, the secondary housing 48 could have a rectangular configuration and the cover 58 could be connected with the base by latch or other fastener. It should be understood that the secondary housing 48 could be formed of materials other than cast copper-free aluminum.

When the covers 52 and 58 for the main and secondary housings are closed, the housing 44 is sealed against entry of gas from the environment around the housing. By preventing entry of gas into the housing 44, ignition of a flammable gas from the environment by a spark in the housing is prevented. This enables the housing 44 to be utilized in any desired environment. Thus, the housing 44 may be used in environments where flammable gases may exist and in environments where there is no possibility of the existence of a flammable gas.

The illustrated monitor station 24 is utilized to monitor gas in the environment around the monitor station. Therefore, one or more sensors for sensing gas are associated with the monitor station 24. Specifically, a combustible gas sensor 62 is connected with the explosion-proof housing 44. The combustible gas sensor 62 is, itself, explosion-proof. In the embodiment of the invention illustrated in FIG. 2, a second gas sensor 66 is connected with the explosion-proof housing 44 and is utilized to detect a second gas, specifically, hydrogen sulfide. The gas sensor 66 is of the intrinsically safe type. The gas sensor 62 is connected with the computer 40 by leads 67 (FIG. 3). The gas sensor 66 is connected with the computer 40 by leads 69.

Although the gas sensors 62 and 66 (FIG. 2) are for specific gases, that is a combustible gas and hydrogen sulfide, it is contemplated that the gas sensors could be for any desired gas. It is also contemplated that either a greater or lesser number of gas sensors could be provided at the monitor station 24. Of course, if the monitor station 24 is to be utilized to monitor an operating condition other than the presence or concentration of a gas, a different type of sensor would be provided at the monitor station. It should be understood that the housing 44 does not have to be explosion-proof if the monitor station 24 is used in an environment in which the danger of an explosion is not a factor.

It is contemplated that the explosion-proof housing 44 may have many different constructions. The specific explosion-proof main housing 46 illustrated in FIG. 2 is commercially available from Adalet, a Scott Fetzer company, of 4801 West 150$^{th}$ Street, Cleveland, Ohio 44135. Of course, it is contemplated that a different type of main housing 46 may be utilized if desired. It is believed that, for cost reasons, it may be desired to use a relatively inexpensive housing 44 which is not explosion-proof in environments where there is little or no possibility of explosion.

Computer Program Revision and Data Entry

During installation and/or subsequent operation of the monitor stations 24, it is contemplated that it may be desired to change the program in the computer 40 (FIG. 3) in each of the monitor stations. However, the monitor stations 24 may be located a substantial distance from each other and from the master station 22. In addition, the monitor stations 24 may be relatively inaccessible.

Assuming that an individual desiring to change the program in a computer 40 (FIG. 3) at a monitor station 24 has traveled to the monitor station, the individual must obtain access to the interior of the main housing 46. Obtaining access to the interior of the main housing 46 (FIG. 2)

requires removal of the fasteners 54 and main cover 52. Access is then provided to the computer 40 to change the program in the computer. Once the program has been changed in the computer, the main cover 52 and fasteners 54 must be reinstalled.

In order to simplify the task of changing the program in a computer 40 at a monitor station 24, it is contemplated that the computer program change may be transmitted from the radio 28 (FIG. 1) at the master station 22 to the radio 36 (FIG. 3) at the monitor station. To affect the computer program change, a radio signal 32 (FIG. 1) is transmitted from the antenna 30 at the master station 22 to an antenna 70 (FIG. 3) at the monitor station 24. The radio signal is transmitted from the antenna 70 to the radio 36 at the monitor station 24. From the radio 36, the computer program change is conducted over leads 72 and/or 74 to the computer 40. The computer 40 then makes the desired change in the program in the computer.

Changing the program in the computer by transmitting the program from the radio 28 at the master station 22 to the radio 36 at the monitor station 24 enables the program in the computer 40 to be changed without an individual traveling to the monitor station 24 and without opening the explosion-proof housing 44. Changing the program in the computer 40 changes the detail sequence of instructions representing the step-by-step procedure that can be implemented by the computer 40 to solve a problem. By changing an algorithm in the computer 40, the sequence of instructions and routines followed during operation of the monitor station 24 to monitor for an operating condition, such as, the sensing of gas, can be changed.

It is contemplated that during operation of the monitor system 20 (FIG. 1), it may be desired to change the set points or values in the computer program. For example, the computer program may provide for an alarm when a predetermined sensed concentration of gas is present. It may be desired to either increase or decrease the magnitude of the concentration of the gas at which the alarm is provided. This is accomplished by changing the set points, that is the high limit value, for the sensed gas in the computer program. Changing the set point or high limit value for the sensed gas in the computer program does not change the computer program itself. Thus, the step-by-step procedure or algorithm utilized by the computer 40 (FIG. 3) to solve a problem is not changed by changing the magnitude of the concentration of the sensed gas required for the computer to trigger an alarm.

Monitor Station

The monitor station 24 includes the explosion-proof main housing 46 and the explosion-proof secondary housing 48 (FIG. 2). The explosion-proof main housing 46 encloses the radio 36 and computer 40 (FIG. 3). In addition, a battery 74 (FIG. 3) and battery charger 76 are enclosed within the explosion-proof main housing 46. The battery charger 76 is connected with a source of electrical energy by conductor 80. In the specific instance illustrated in FIG. 3, the battery charger 76 is connected with a 110-volt alternating current source of electrical energy by the conductor 80. The conductor 80 is enclosed within a conduit 82. Suitable seals are provided in the conduit to prevent communication of gas through the conduit to the explosion-proof main housing 46.

A junction box or hub 86 (FIG. 2) is provided in the secondary housing 48 to connect the secondary housing with the main housing 46. The rectangular junction box 86 has a plug which may be removed to enable an explosion-proof alarm to be mounted on the junction box. The explosion-proof alarm may be of the audible and/or visible type. A conduit 88 connects the junction box 86 with the remainder of the secondary housing 48. The secondary housing 48 is connected with the gas sensor 62 by a conduit 90 and is connected with the gas sensor 66 by a conduit 92.

The secondary housing 48 encloses a terminal which may be plugged into a data entry device, such as a laptop computer, when the cover 58 is removed from the secondary housing. The terminal enclosed by the secondary housing 48 is connected with the computer 40 (FIG. 3) in the main housing 46. By plugging the data entry device (laptop computer) into the terminal enclosed by the secondary housing 48, the data entry device is connected in communication with the computer 40 in the main housing 46 in over suitable leads (not shown).

It is contemplated that the terminal in the secondary housing 48 will be utilized to initially enter data corresponding to various set points in a program for the computer 40 when the monitor station 24 is initially installed. After the monitor station 24 has been installed, it is believed that it will probably be desired to change the data corresponding to the various set points in the computer program by transmitting the changes in the data from the radio 28 at the master station 22 to the radio 36 and computer 40 at the monitor station. This eliminates the need to travel to the monitor station 24 and open the explosion-proof housing 44.

The gas sensor 62 is explosion-proof and therefore can be connected with the explosion-proof housing 44 without impairing the explosion-proof characteristics of the housing. However, the gas sensor 66 is intrinsically safe. The housing 44 is capable of withstanding any explosion of gas or vapor that may occur within the housing. In addition, the housing 44 is also effective to prevent the ignition of gas or vapor surrounding the housing by sparks, flashes, and/or an explosion of gas or vapor within the housing.

During operation the radio 36, computer 40, battery charger 76, battery 74, and/or gas sensors 62 and 66, the housing 44 is at a temperature such that gas or vapor within the atmosphere surrounding the housing will not be ignited. Since the gas sensor 66 is only intrinsically safe, a suitable seal, that is, a conduit seal hub 96 (FIG. 2) is provided between the gas sensor 66 and the secondary housing 48. A suitable seal or conduit seal hub 98 is also provided between the antenna 70 and the explosion-proof main housing 46.

Operation of Gas Monitor Station

The sensors 62 and 64 are effective to provide analog output signals corresponding to the concentration of selected gases in the atmosphere adjacent to the sensors. Thus, the sensor 62 is effective to provide an analog output signal corresponding to the concentration of a selected combustible gas. Similarly, the gas sensor 66 provides an analog output signal corresponding to the concentration of hydrogen sulfide in the atmosphere. Of course, the gas sensor 66 could be constructed so as to sense a different gas if desired.

The output from the gas sensors 62 and 66 is transmitted over the leads 67 and 69 to the computer 40 in the main housing 46. An analog-to-digital converter in the computer 40 converts the analog output signals from the sensors 62 and 66 to digital signals. The digital signals, corresponding to the analog output signals from the sensors 62 and 66 are transmitted to a microprocessor in the computer 40.

When the microprocessor in the computer 40 detects that a predetermined concentration of either one of the two gases sensed by the sensors 62 and 66 is present in the atmosphere, the microprocessor initiates transmission by the radio 36 to the radio 28 at the master station 22. The computer 40 is effective to initiate transmission by the radio 36 of a signal to the master station 22 in response to detection of either one of two predetermined concentrations of a selected gas by the sensor 62. Similarly, the computer 40 is effective to cause the radio 36 to transmit signals to the master station 22 in response to detection of either one of two predetermined concentrations of a gas (hydrogen sulfide) by the gas sensor 66.

When the sensed concentration of a selected gas by either one of the two gas sensors 62 or 66 reaches a first, relatively low, concentration, the computer 40 initiates radio transmission of a HI signal to the radio 28 in the master station 18. The HI signal identifies the gas and indicates that the concentration of the gas has increased to a level which is of interest. When the concentration of the gas sensed by the sensor 62 or 66 increases to a second level, the computer 40 initiates operation of the radio 36 to transmit a HIHI alarm signal to the radio 28 in the master station 22. This HIHI alarm signal indicates to personnel at the master station 22 that the concentration of either the gas detected by the sensor 62 or the gas detected by the sensor 66 has reached a level of concern and that suitable action should be taken. The HIHI alarm signal also indicates to the personnel at the master station 22 the identity of the gas which caused the alarm to be sent.

In order to promote understanding of the situation by personnel at the master station 22, the radio 36 transmits data which is indicative of the actual concentration of gas in the atmosphere adjacent to the gas monitor station 24. Thus, when either a HI signal or a HIHI signal is transmitted by the radio 36 to the radio 28 in the master station 22, the signal identifies the gas, that is either the gas sensed by the sensor 62 or the gas sensed by the sensor 66 and indicates the actual concentration of the gas.

The data transmitted by the radio 36 to the master station 22 is displayed at the master station and indicates the actual concentration of the selected gas which caused the transmission of the signal, that is the gas sensed by either the sensor 62 or the sensor 66. The visual and/or audible alarms may be activated at the master station 22 when the data transmitted by the radio 36 corresponds to either a HI alarm or a HIHI alarm. Of course, visual and/or audible alarms may be provided when the data transmitted by the radio 36 corresponds to other predetermined conditions. In addition, visual and/or audible alarms may be provided at the gas monitor station 24. The alarms at the gas monitor station 24 may be explosion-proof and mounted on the explosion-proof housing 44.

Personnel at the master station 22 can change the data stored in the computer 40 at the monitor stations 24 to change the sensed concentrations of gas which cause the computer 40 to initiate a HI alarm and/or a HIHI alarm. When the data stored in the computer 40 is to be changed, a data change code signal is transmitted from the radio 28 at the master station 22 to the radios 36 in the monitor stations 24. In response to receipt of the data change code, the computers 40 at the monitor stations 24 make the desired change in the computer program set points corresponding to the HI alarm and/or HIHI alarm. After the computer program set points have been changed, the computer 40 initiates a HI alarm and/or a HIHI alarm when gas concentrations corresponding to the new set point values are sensed.

It is contemplated that personnel at the master station 22 may want to know when there is a predetermined variation in the sensed quantity of a selected gas in the atmosphere at the gas monitor station 24. Thus, it is believed that when there is a predetermined variation in the sensed quantity of the gas sensed by the sensor 62, the personnel at the master station 22 would want to be notified. Similarly, when there is a predetermined variation in the quantity of the gas sensed by the sensor 66, it is believed that the personnel at the master station 22 will also want to be notified. Therefore, the computer 40 determines when the sensed concentration of the gas sensed by the sensor 62 and/or the gas sensed by the sensor 66 that the gas monitor station 24 has either increased or decreased by a predetermined amount.

When the computer 40 determines that the predetermined variation in the sensed concentration of either one or both of the selected gases has occurred, the computer initiates any alarm provided at the gas monitor station 24 and transmission by the radio 36 to the master station 22. The computer 40 initiates transmission of a signal indicating the magnitude of the change in the concentration of either one or both of the selected gases. The predetermined variation and concentration of either one or both of the selected gases may occur when the concentration of a selected gas has either increased or decreased by a predetermined amount.

The magnitude of the variation in the sensed quantity of gas required to cause the computers 40 at the monitor stations 24 to initiate radio transmission to the master station 22 can be changed without traveling to the monitor stations. When the magnitude of the variation in the sensed quantity of gas required to initiate an alarm is to be changed, the radio 28 at the master station transmits a data change code signal to the radios 36 in the monitor stations 24. In response to the data change code signal, the computers 36 change the magnitude of the variation in the sensed quantity of gas in accordance with the data transmitted from the master station 22. Therefore, the magnitude of the variation in the quantity of gas sensed by the sensors 62 and/or 66 required to initiate an alarm can be changed without opening the explosion-proof housing 44.

It is contemplated that transient conditions may result in an instantaneous increase and/or decrease in the concentration of the gas sensed by the sensor 62 and/or the gas sensed by the sensor 66 in the environment around the gas monitor station 24. Thus, a roughly small puff of either one or both of the two gases may be blown past the gas sensors 62 and 66 at the gas monitor station 24. In order to prevent the transmission of data from the gas monitor station 24 to the master station 22 in response to these transient conditions or puffs of the selected gas, the computer 40 is effective to average the input received from either one or both of the sensors 62 and 66 over a predetermined period of time. The period of time over which the input is averaged may be the same for both gas sensors 62 and 66 or may be different.

The period of time over which the microprocessor averages the input from the gas sensor 62 and the period of time over which the microprocessor averages the input from the sensor 66 are relatively short to enable the gas monitor station 24 to quickly respond to conditions which are not transient. Thus, the computer 40 may average the input from the sensors 62 and 66 over a period of time of 30 seconds or less. For example, the computer 40 may average the data received from the gas sensor 62 over a period of approximately 10 seconds and average the data received from the gas sensor 66 over a period of approximately 12 seconds.

Before the computer 40 initiates transmission with the radio 36 of an alarm signal, whether it is a HI signal or a HIHI signal to the master station, the level of concentration of the selected gas in the atmosphere adjacent to the gas monitor station will have been present for a short period of time, for example 10 or 12 seconds. By averaging the outputs from the gas sensors 62 and 66 over short periods of time, false or spurious alarms in response to transient conditions are avoided.

The period of time over which the outputs from the gas sensors 62 and/or 66 are averaged can be changed from the master station 22. To change the period of time over which outputs from the gas sensors are averaged, the radio 28 at the master station 22 transmits a data change code signal to the monitor stations 24. In response to the data change code signal, the computers 40 at the monitor stations 24 change the period of time over which sensor readings are averaged.

It is contemplated that it may be desired to have a short-term exposure limit (STEL) alarm. A short-term exposure limit alarm averages exposure level over a predetermined length of time. When a multiple of the average sensed concentration of a selected gas and the elapsed time over which the average sensed concentration is determined to exceed a predetermined magnitude, an alarm signal is initiated. Thus, when a multiple of the average concentration of gas sensed by the sensor 62 and the elapsed time over which the average sensed concentration was determined exceeds a predetermined magnitude, the computer 40 initiates operation of the radio 36 to transmit a signal to the master station 22. Similarly, when a multiple of the average concentration of gas sensed by the sensor 66 and the elapsed time over which the average sensed concentration is determined exceeds a predetermined magnitude, the computer 40 initiates transmission with the radio 36 to inform the master station 22 that a short-term exposure limit has been exceeded.

For example, the average short-term exposure limit for the gas sensor 62 could be set at 0.3 parts per million (ppm) over a period of time, for example, 15 minutes. The multiple of the average concentration of the selected gas (0.3 ppm) over the period of selected time (15 minutes) is 4.5. Therefore, if there is an average exposure of 0.3 ppm of the selected gas for a period of 15 minutes, the computer 40 initiates transmission to the master station 22 with the radio 36.

The time and/or multiple of average sensed gas concentration and time for the short-term exposure limit alarm can be changed from the master station 22. When either one or both of these values are to be changed in the computer programs at the monitor stations 24, a data change code signal is transmitted from the master station 22 to the monitor stations 24. The data change code signal instructs the monitor station computers 40 to change the time and/or multiple for the short-term exposure limit alarm. The data change code signal indicates the desired new values for the time and/or multiple for the short-term exposure limit alarm.

It is contemplated that it will be desired to have some check at the master station 22 to determine whether or not the gas monitor station 24 is functioning. This is particularly true when circumstances are such that the computer does not initiate transmission with a radio 36 in response to a change in sensed concentrations of the selected gases or a change in status for a long period of time. Therefore, when the computer 40 determines that a predetermined maximum length of time has elapsed since the last transmission was made with the radio 36, the computer 40 initiates transmission with the radio 36 to the master station 22.

For example, if a time period of 30 minutes passes after transmission is made by the radio 36 to the master station 22, the computer 40 initiates transmission with the radio to the master station. This informs the master station 22 that the gas monitor station 24 is still functioning. The master station 22 then resets a timer for the maximum length of time between communications from the gas monitor station 24.

If more than the predetermined time period, for example, sixty-five minutes, passes between communications from the gas monitor station 24 to the master station 22 an alarm is provided at the master station. This alarm indicates to personnel at the master station that the gas monitor station 24 has not transmitted to the master station for more than the predetermined period of time. Personnel at the master station 22 can then initiate an inspection of the gas monitor station 24 to determine why the gas monitor station 24 had not transmitted to the master station for more than the predetermined period of time.

The computer 40 is also effective to determine when the power level, that is the output voltage, from the battery 74 below a predetermined level. Thus, the output voltage of the battery 74 is transmitted to the computer 40. When this output voltage falls below a predetermined level, for example, twelve volts (direct current), the computer 40 initiates a transmission with the radio 36 to the master station 22 to indicate that the output of the battery is below a desired level. When they are not being used, the computer 40 and radio 36 are shut down to a de-powered or standby condition to minimize the load on the battery 74.

The computer 40 also initiates transmission with the radio 36 to the master station 22 if the output from the battery 74 changes by more than a predetermined amount. For example, if the battery voltage should increase or decrease by more than 0.5 volts within the predetermined period of time, the computer 40 will initiate transmission with the radio 36 to indicate to the master station 22 that there has been a change in battery voltage.

It should be understood that when the computer 40 initiates transmission of the radio 36 to the master station 22, the radio is effective to transmit: (1) data identifying the gas or gases which caused the transmission to be initiated, and (2) data which indicates the magnitude of the condition which is present. For example, when the concentration of the selected gas sensed by the sensor 62 in the atmosphere at the gas monitor station 24 exceeds a concentration necessary to trigger the HI alarm, the computer 40 initiates transmission with the radio 36 to transmit data indicative of the actual sensed concentration of the selected gas by the sensor 62 in the environment adjacent to the gas monitor station 24. Similarly, when the gas sensor 66 senses that the concentration of a selected gas in the atmosphere at the gas monitor station 24 exceeds a concentration to trigger a HI alarm, the computer 40 initiates transmission with the radio 36 to transmit data indicative of the actual sensed concentration of the gas in the environment adjacent to the gas monitor station 24. When the computer 40 initiates operation of the radio 36 in response to a predetermined variation in the concentration of either one or both of the selected gases in the atmosphere at the gas monitor station 24, data indicative of the actual concentration of the selected gas and/or gases and the actual variation in the concentration of a selected gas and/or gases is transmitted from the gas monitor station 24 to the master station 22 by the radio 36.

The radio 36, computer 40, and gas sensors 62 and 66 at the gas monitor station 24 cooperate with each other in the same manner which is disclosed in U.S. patent application Ser. No. 09/854,748 having a filing date of May 14, 2001, filed by Cornelius P. Dungan and entitled Apparatus and Method for Wireless Gas Monitoring. The disclosure in the aforementioned U.S. patent application Ser. No. 09/854,748 is hereby incorporated herein in its' entirety by this reference thereto.

Monitor Station—Second Embodiment

The monitor station 24 in FIGS. 1–3 is connected with 110-volt source of electrical power by a conductor 80 (FIG. 3). The embodiment of the monitor station illustrated in FIG.

Figure 4:
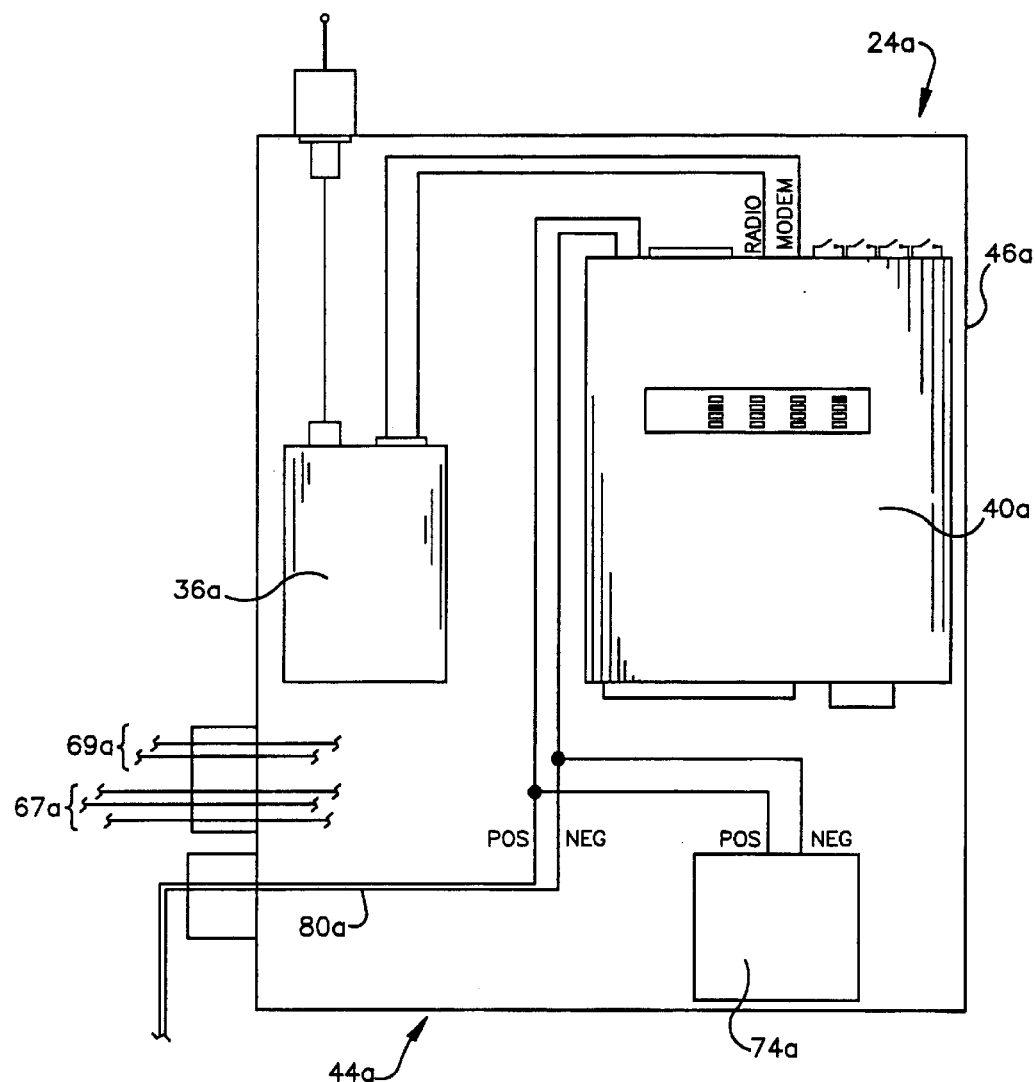
FIG. 4 is a schematic illustration, generally similar to FIG. 3, a second embodiment of the monitor station, the monitor station being adapted to be connected with a solar panel.

4 is generally similar to the monitor station illustrated in FIGS. 1–3. However, the monitor station of FIG. 4 is powered from a solar panel rather than 110-volt source of electrical power. Since the monitor station of FIG. 4 has the same general construction and mode of operation as the monitor station 24 of FIGS. 1–3 similar numerals will be utilized to designate similar components, the suffix letter "a" being associated with the numerals of FIG. 4 to avoid confusion.

A monitor station 24a includes an explosion-proof housing 44a having an explosion-proof main housing 46a. An explosion-proof secondary housing, having the same construction as the explosion-proof secondary housing 48 of FIG. 2, is connected with the explosion-proof main housing 46a in the same manner as previously explained in conjunction with the embodiment in the invention illustrated in FIGS. 1–3. The housing 44a is sealed against entry of gases or vapors in the same manner as previously described in conjunction with the embodiment of the invention illustrated in FIGS. 1–3. However, it should be understood that the explosion-proof housing 44a could have a construction which is different than the specific construction previously described in conjunction with FIGS. 1–3. If desired, a housing which is not explosion-proof could be substituted for the housing 44a.

The explosion-proof housing 44a encloses a radio 36a and a computer 40a. A battery 74a is enclosed within the explosion-proof housing 44a.

In accordance with a feature of the embodiment of the invention illustrated in FIG. 4, the battery 74a is connected with a solar panel (not shown) by a conductor 80a. The solar panel may be monitored at the gas monitor station 24a and cooperate with the battery 74a and computer 40a in the same manner as is disclosed in the aforementioned U.S. patent application Ser. No. 09/854,748 filed May 14, 2001 by Cornelius P. Dungan. It is contemplated that it will be desired to use a solar panel to power the battery 74a when the gas monitor station 24a is located at a location where a 110 volt AC source of power is not readily available.

Monitor Station—Third Embodiment

In the embodiments of the monitor stations illustrated in FIGS. 1–4, a secondary housing 48 (FIG. 2) is opened to provide access to a computer terminal through which data is entered into a computer in a main housing 46. To enter data, a laptop computer or similar device is connected with the terminal after opening the secondary housing 48. In the embodiment in the invention illustrated in FIG. 5, data entry is provided at the computer within the main housing. Since the embodiment of the invention illustrated in FIG. 5 is generally similar to the embodiments of the invention illustrated in FIGS. 1–4, similar numerals will be utilized to designate similar components, the suffix letter "b" is associated with the numerals of FIG. 5 to avoid confusion.

Figure 5:
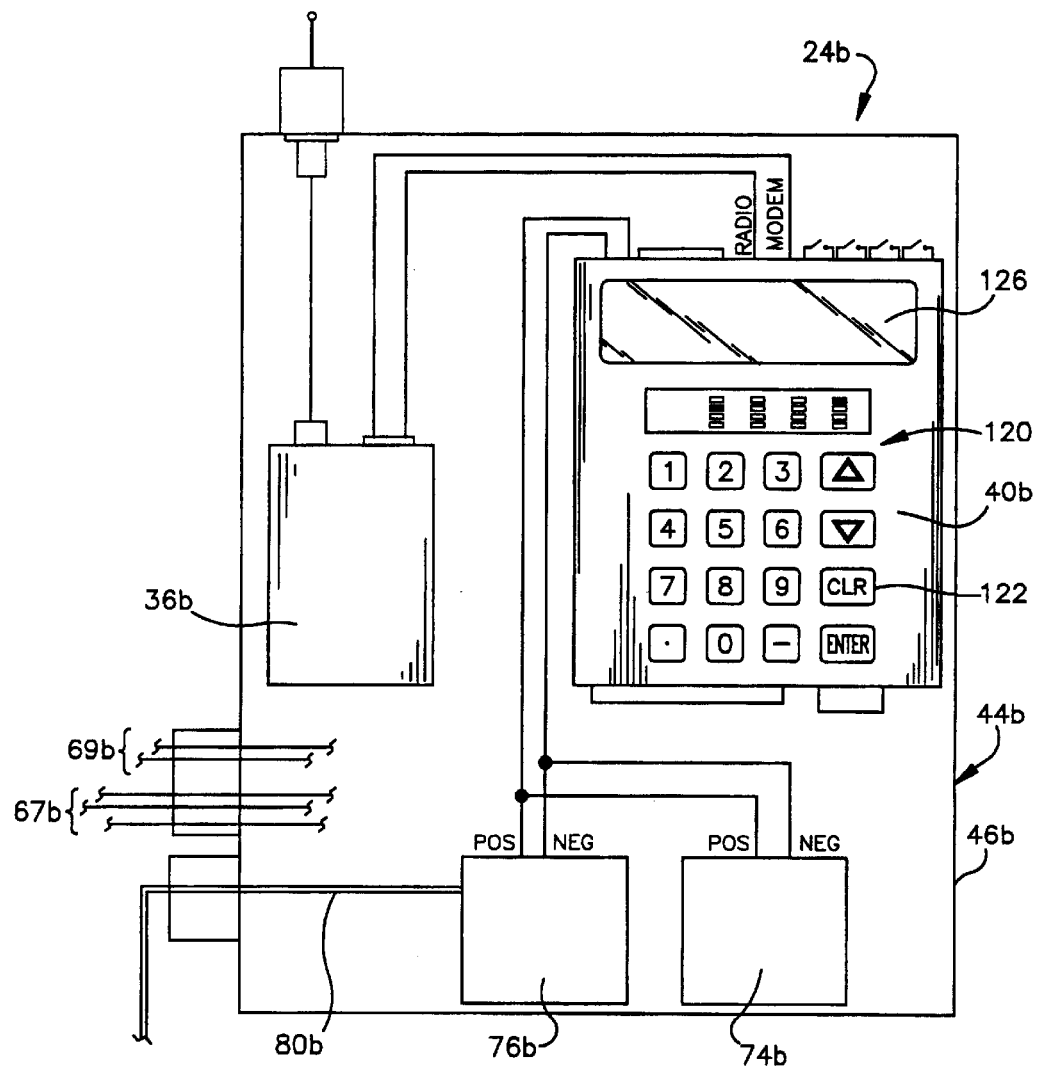
FIG. 5 is a schematic illustration, generally similar to FIGS. 3 and 4, illustrating a third embodiment of a monitor station, a computer at the monitor station having manually actuatable data entry apparatus.

A monitor station 24b includes an explosion-proof housing 44b having a main housing 46b (FIG. 5). A radio 36b and computer 40b are disposed within the explosion-proof housing 44b. A battery 74b and battery charger 76b are also disposed in the housing 44b. A conductor 80b connects the battery charger 76b with a source of electrical energy, specifically, a source of 110 volt AC current. Leads 67b and 69b connect the computer 40b with sensors corresponding to the sensors 62 and 66 of FIG. 2. The radio 36b, sensors, and computer 40b cooperate in the same manner as previously described in conjunction with the embodiment of the invention illustrated in FIGS. 1–3.

In accordance with a feature the embodiment of the invention illustrated in FIG. 5, data entry apparatus 120 is mounted on a housing for the computer 40b. The data entry apparatus 120 includes a keypad 122 which is manually actuated when the explosion-proof housing 44b is in an open condition. Manual actuation of the keypad 122 is effective to enter data into the computer 40b at the gas monitor station 24b.

A display 126 is disposed on the computer 40b directly above the keypad 122. When the data entry apparatus 120 is actuated to enter data into the computer 40b, indicia at the display 126 changes to indicate the data entered. This enables the individual entering the data by manually actuating the keypad 122 to view the display 126 and determine whether or not the data was correctly entered. Of course, if the data was not correctly entered, the individual entering the data would actuate the keypad 122 to revise the data. The display 126 also sets forth indicia which prompts an individual actuating the keypad 122 to enter the required data. The display 126 is effective to increase the user-friendliness of the data entry apparatus 120.

Rather than having a manually actuated keypad 122, the computer 40b could be provided with a data entry apparatus which is remotely actuated For example, a computer 40b could include a plurality of switches which are contained within a separate housing for the computer 40b and are magnetically actuated. Alternatively, a remote control unit, similar to the remote control units commonly utilized in association with television sets, could be utilized to actuate the data entry apparatus 120.

It is contemplated that the data entry apparatus 120 could have the same construction as the data entry apparatus disclosed in the aforementioned U.S. patent application Ser. No. 09/854,748 filed May 14, 2001 by Cornelius P. Dungan and entitled Apparatus and Method for Wireless Gas Monitoring. The disclosure in the aforementioned application Ser. No. 09/854,748 has been and hereby is incorporated herein in its' entirety by this reference thereto.

Sensors

In the embodiments of the invention illustrated in FIGS. 1–5, the monitor stations 24 have been effective to sense one or more selected gases in an environment around the monitor station. However, it is contemplated that the monitor stations 24 could be utilized to monitor for operating conditions other than the presence of a selected gas. Examples of sensors which could be utilized in association with a monitor station 24, other than the gas sensors 62 and 66 (FIG. 2), are illustrated in FIGS. 6–9. It should be understood that the sensors of FIGS. 6–9 may be utilized together or separately. One or more of the sensors of FIGS. 6–9 may be used at a monitor station with or without one or more gas sensors.

Figure 6:
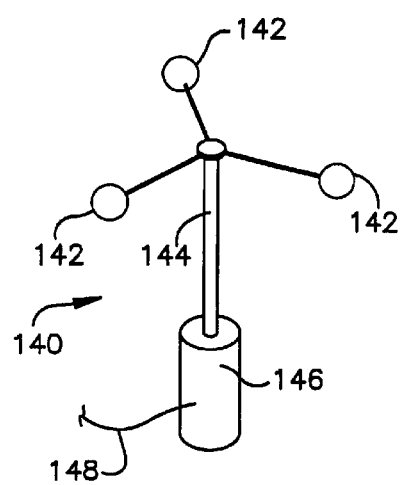
FIG. 6 is a schematic illustration of a sensor for use at a wind speed monitor station.

A sensor assembly 140 for sensing wind speed is illustrated schematically in FIG. 6. The sensor assembly 140 is an anemometer having cup-shaped shells 142. The cup-shaped shells 142 have a rigid hemispherical construction with circular openings for collecting wind. The cup-shaped shells 142 are fixedly connected with a shaft 144. A shaft 144 is connected with a sensor 146.

The sensor 146 is of the tachometer generator type and senses the speed of rotation of the shaft 144. The output from the sensor 146 is transmitted over a lead to a computer corresponding to the computer 40 of FIG. 3. The sensor assembly 140 may have a construction which is similar to the construction illustrated in U.S. Pat. No. 5,918,276. It should be understood that a different known type of wind sensor could be utilized if desired. For example, the wind sensor assembly 140 could have a construction corresponding to U.S. Pat. No. 4,615,214.

A sensor assembly 152 (FIG. 7) may be provided in association with a monitor station 24 to sense the flow of fluid in a conduit 154. The sensor 152 includes an impeller 156 which is disposed in the conduit 154 and is connected with a suitable sensor which senses the rate of rotation of the impeller under the influence of fluid flow through the conduit 154. The fluid flowing through the conduit 154 may be either a gas or a liquid. Rotation of the impeller 156 causes a tachometer generator type sensor 158 to provide an output signal which is conducted over a conductor 160 to a computer, corresponding to the computer 40 of FIG. 3, at the monitor station.

Figure 7:
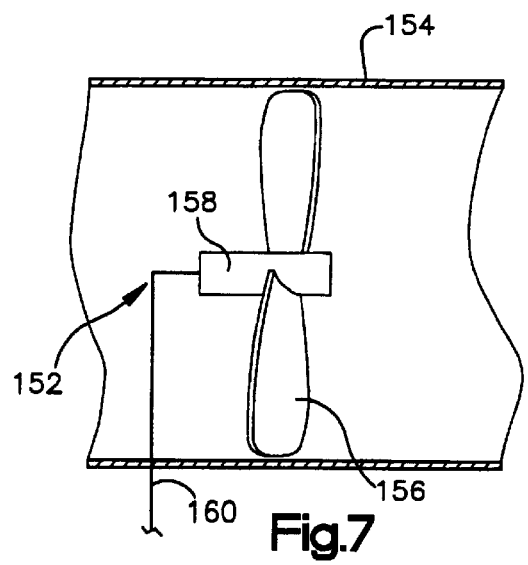
FIG. 7 is a schematic illustration of a fluid flow sensor for use at a fluid flow monitor station.
Figure 8:
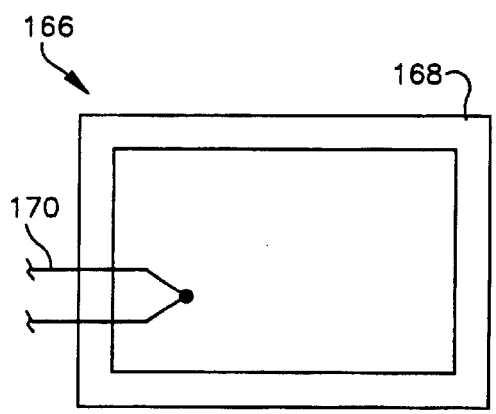
FIG. 8 is a schematic illustration of a temperature sensor for use at a temperature monitor station.
Figure 9:
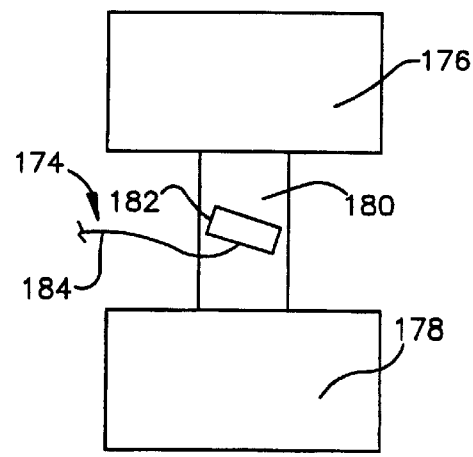
FIG. 9 is a schematic illustration of a pressure and/or force sensor for use at a pressure and/or force monitor station.

The sensor assembly 152 may have a construction which is different from the specific instruction illustrated in FIG. 7. For example, the sensor assembly 152 may have a construction which corresponds to the construction illustrated in U.S. Pat. No. 5,625,155 or U.S. Pat. No. 4,232,548.

A sensor assembly 166 (FIG. 8) may be provided to sense temperature. The sensor assembly 166 is connected with a container 168 in which temperature is to be sensed. A thermocouple 170 is an output which varies as a function of variations in the temperature within the container 168. The output from the thermocouple 170 may be submitted to a computer, corresponding to the computer 40 of FIG. 3, at a monitor station.

A sensor assembly 174 (FIG. 9) is utilized to sense variations in pressure or force transmitted between upper and lower members 176 and 178 through an intermediate member 180. The sensor assembly 174 includes a load cell 182 formed by strain gauges. The output from the load cell 182 is transmitted through a conductor 184 to a computer, corresponding to the computer 40 of FIG. 3.

It is contemplated that any one of the sensor assemblies 140, 152, 166 or 174 may be provided at a monitor station. Alternatively, a combination of two or more of the sensor assemblies 140, 152, 166 and 174 may be provided at a monitor station 24. If desired, a gas sensor, similar to the gas sensors 62 and 66 of FIG. 2, may be utilized in association with one or more of the sensor assemblies 140, 152, 166 and 174.

It should be understood that the sensor assemblies 140, 152, 166 and 174 and the gas sensors 62 and 66 are merely examples of many different known sensors which may be utilized at a monitor station 24. It is contemplated that any known sensor may be utilized to sense any desired operating condition.

Portable Monitor Station

It is contemplated that the monitor stations 24 of FIGS. 1–5 will be moved to a location and be more or less permanently mounted at that location. The monitor station of FIG. 10 is intended to be moved between various locations. Thus, the monitor station of FIG. 10 may be positioned at a first facility during operations at that facility. The monitor station may subsequently be moved to a second facility and used at the second facility during operation of the second facility. Since the monitor station of FIG. 10 has the same general construction and mode of operation as the monitor stations of FIGS. 1–5, similar numerals will be utilized to designate similar components, the suffix letter "c" being associated with the numerals of FIG. 10 to avoid confusion.

A monitor station 24c includes a portable housing 44c having a handle 200. The housing 44c and handle 200 result in the portable monitor station 24c having an exterior appearance which is generally similar to the exterior appearance of an attaché case or small suitcase. The relatively compact size of the portable monitor station 24c and the handle 200 facilitate carrying of the monitor station 24c from one location to another location.

The portable monitor station 24c includes a radio 36c and computer 40c which are enclosed within the housing 44c (FIG. 10). A battery 74c is disposed in the housing to provide a portable power source for the radio 36c and computer 40c. A battery charger 76c is also provided within the housing 44c. A power cord or conductor 80c is connectable with a 110-volt source of power to enable the charger 76c to charge the battery 74c in a known manner.

A gas sensor 62c is disposed within the housing 44c. An inlet 204 is connected with the gas sensor 62c and is exposed to the environment around the housing 44c. A gas outlet 206 is also connected with the sensor 62c and is exposed to the environment around the housing 44c. A small fan or other device is provided in association with the sensor 62c to induce a flow of gas through the inlet 204 into the sensor 62c and through the outlet 206 to the environment around the portable housing 44c. It is contemplated that the gas sensor 62c may have any one of many known constructions.

In accordance with one of the features of the embodiment of the invention illustration in FIG. 10, a receiver 42 for a global positioning system is mounted on the housing 44c. The global positioning system receiver 42 is connected with the computer 40c. The global positioning system receiver 42 receives signals from satellites and provides an output which is indicative of the location of the monitor station 24c. In response to a signal from a master station, corresponding to the master station 22 of FIG. 1, the computer 40c affects the operation of the radio 36c to transmit a signal from an antenna 70c to the master station. This signal indicates to the master station the position of the portable monitor station relative to the master station. The receiver 42 has a known construction and may function in a manner similar to that disclosed in U.S. Pat. No. 4,785,463 and/or U.S. Pat. No. 5,884,214.

Data entry apparatus 120c is mounted on a housing for the computer 40c. The data entry apparatus 120c includes a keypad 122c which is manually actuated when the housing 44c is in an open condition. A latch 214 is provided to maintain the housing in a closed position. However, the latch 214 can be manually actuated to enable the housing 44c to be opened in a known manner. When the housing 44c is open in a known manner, an individual may manually enter data into the computer 40c by actuating the keypad 122c in the same manner as was described in the aforementioned U.S. patent application Ser. No. 09/854,748 filed May 14, 2001 by Cornelius P. Dungan.

If desired, the portable housing 44c may be constructed so as to be explosion-proof. When the housing 44c is to be explosion-proof, a plurality of latches 214 or other fasteners may be used to securely seal the housing against entry of gas from the environment around the portable monitor station 24c. Of course, gas would still enter the housing 44c through the gas inlet 204 and be discharged from the housing through the gas outlet 206.

A second sensor is connected with the computer 40c by a conductor 220 (FIG. 10). The second sensor may be effective to sense wind speed and/or direction at a location where the portable monitor station is positioned. Any one of the sensors of FIGS. 6–9 could be connected with the computer 40c (FIG. 10) by the conductor 220.

Any one of the features previously described in conjunction with FIGS. 1–9 may be used with the portable monitor station 40c of FIG. 10.

Summary

In view of the foregoing description, it is apparent that the present invention provides a new and improved method and apparatus 20 for monitoring for one or more selected conditions. The selected conditions may be the presence and/or concentration of a selected gas, wind speed and/or direction, the rate of fluid flow, temperature, pressure, and/or force. Of course, the apparatus could be utilized to sense for other conditions, or combinations of conditions, if desired.

A plurality of monitor stations 24 may be provided at spaced apart locations. A programmable computer 40 may be connected with a radio 36 and a sensor 62 and/or 66 at each of the monitor stations. During use of the apparatus 20, a computer program change may be transmitted from a master station radio 28 to the radio 36 in at least one of the monitor stations 24. In addition, or alternatively, data may be transmitted from the radio 28 at the master station 22 to the radios 36 at each of the monitor stations 24. The data transmitted to the monitor stations 24 may be utilized in computers 40 at the monitor stations.

The computer 40 and radio 36 at each of the monitor stations 24 may be enclosed in an explosion-proof housing 44 which is sealed against the entry of gas from the atmosphere around the monitor station. Whether or not the housing is sealed against entry of gas, the housing may have a relatively large main opening which is closed with a relatively large main cover 52 and a relatively small secondary opening which is closed with a relatively small secondary cover 58. Data relating to gas or other selected operating condition to be monitored, may be entered into the computer 40 by opening the relatively small secondary cover 58 while the relatively large main cover 52 remains closed.

Portable monitor stations 24c may be provided. A global positioning system receiver 42 may be provided at each of the portable monitor stations. The global positioning system receivers 42 enable computers 40c in the portable monitor stations 24c to inform a master station 22 of the locations of the portable monitor stations 24c.

What is claimed is:

1. A method of monitoring for a selected gas from a potential source of the selected gas, said method comprising the steps of providing a plurality of gas monitor stations at locations spaced from the potential source of the selected gas and from a master station, said step of providing a plurality of gas monitor stations includes providing a computer connected with a radio and a sensor at each of the gas monitor stations, transmitting data relating to the selected gas from a radio at the master station to the radios at each of the gas monitor stations, storing the data transmitted from the master station and relating to the selected gas in the computers at each of the gas monitor stations, sensing atmosphere adjacent to each of the gas monitor stations, and transmitting a signal from the radio at anyone of the gas monitor stations to the radio at the master station in response to sensing of a concentration of the selected gas which is a function of the data transmitted from the master station to the one gas monitor station.

2. A method as set forth in claim 1 further including the steps of determining at each of the gas monitor stations the length of time which has elapsed since transmission of a radio signal, and transmitting a radio signal from anyone of the gas monitor stations to the master station upon determining that a predetermined period of time has elapsed since transmission of a radio signal.

3. A method as set forth in claim 1 wherein said step of transmitting data from the master station to each of the gas monitor stations includes transmitting data relating to an average permissible magnitude of concentration of the selected gas over a predetermined period of time, and transmitting a radio signal from anyone of the gas monitor stations to the master station in response to sensing of an average concentration of the selected gas greater than the permissible magnitude.

4. A method as set forth in claim 1 further including the step of eliminating the effect of transient variations in the concentration of the selected gas in the atmosphere adjacent to the gas monitor stations by averaging the sensed magnitude of the selected gas over a period of time of thirty seconds or less.

5. A method as set forth in claim 1 wherein a radio at each gas monitor station utilizes electrical energy at a first rate when the radio is in a transmit mode and is transmitting to the master station and utilizes electrical energy at a second rate which is less than the first rate when the radio is in a standby mode, said method further includes maintaining the radio at each of the gas monitor stations in the standby mode except when the radio is transmitting.

6. A method as set forth in claim 1 wherein said step of transmitting data from the master station to each of the gas monitor stations includes transmitting data relating to a moving average gas concentration over a predetermined length of time, said method further includes determining when the moving average of sensed concentration over a predetermined length of time of the selected gas in the atmosphere adjacent to one of the monitor stations exceeds a predetermined magnitude, and transmitting a radio signal to the master station in response to a determination that the moving average concentration of the selected gas over the predetermined length of time exceeds the predetermined magnitude.

7. A method as set forth in claim 1 further including the steps of transmitting a predetermined input voltage to a sensor at each of the gas monitor stations, transmitting an output voltage from the sensor at each of the gas monitor stations, determining if the sensor at anyone of the gas monitor stations should be replaced as a function of the magnitude of the output voltage, and transmitting a radio signal from the radio at a gas monitor station to the radio at the master station in response to a determination that a sensor should be replaced.

8. A method as set forth in claim 1 further including the steps of transmitting a computer program change from the master station radio to the radio in at least one of the gas monitor stations, and changing a program in at least one of the computers in at least one of the gas monitor stations in accordance with the computer program change transmitted by radio from the master station.

9. A method as set forth in claim 8 further including the steps of transmitting a change in magnitude of a set point in a computer program from the radio in the master station to the radio in at least one of the gas monitor stations, and changing the magnitude of the set point in the program in the computer in at least one of the gas monitor stations without changing the program in the computer.

10. A method as set forth in claim 1 wherein said step of providing a plurality of gas monitor stations includes enclosing the computer and radio at each of the gas monitor stations in the housing which is sealed against entry of gas from the atmosphere around the gas monitor station.

11. A method of monitoring for a selected gas from a potential source of the selected gas, said method comprising the steps of providing a plurality of gas monitor stations at locations spaced from the potential source of the selected gas and from a master station, said step of providing a plurality of gas monitor stations includes providing a computer connected with a radio and a sensor at each of the gas monitor stations and enclosing at least the computer and radio at each of the gas monitor stations with an explosion-proof housing which is sealed against entry of gas from atmosphere adjacent to each of the gas monitor stations, entering data relating to the selected gas into the computer at each of the gas monitor stations by transmitting data from a location outside of the explosion-proof housing at each of the gas monitor stations to the computer in the explosion-proof housing, sensing atmosphere outside of the explosion-proof housing at each of the gas monitor stations while the explosion-proof housing at each of the gas monitor stations is sealed against entry of gas from the atmosphere adjacent to each of the gas monitor stations, and transmitting a radio signal from the radio in the sealed explosion-proof housing at anyone of the gas monitor stations to a master station in response to sensing of the selected gas in conditions which are a function of the data entered into the computers at the gas monitor stations.

12. A method as set forth in claim 11 wherein said step of entering data relating to the selected gas by transmitting data from outside of the explosion-proof housing at each of the gas monitor stations includes transmitting data from a data input terminal disposed outside of the explosion-proof housing along conductors connected to the computer disposed inside the explosion-proof housing at each of the gas monitor stations.

13. A method as set forth in claim 11 wherein said step of enclosing at least the computer and radio at each of the gas monitor stations with an explosion-proof housing includes enclosing at least the computer and radio at each of the gas monitor stations with an explosion proof housing having a relatively large main opening which is closed with a relatively large main cover and a relatively small secondary opening which is closed with a relatively small secondary cover, said step of entering data relating to the selected gas includes opening the relatively small cover and interconnecting a data input device disposed outside the explosion-proof housing and the computer disposed inside the explosion-proof housing while the main cover is closed and the small cover is open.

14. A method as set forth in claim 11 wherein said step of enclosing at least the computer and radio at each of the gas monitor stations with an explosion-proof housing includes enclosing the computer and radio at each of the gas monitor stations with an explosion-proof housing which is operable between an open condition in which an interior of the explosion-proof housing is in fluid communication with atmosphere adjacent to the gas monitor station and a closed condition in which the interior of the explosion-proof housing is sealed against entry of gas from atmosphere adjacent to the gas monitor station, said step of entering data relating to the selected gas is performed with the explosion-proof housing in the open condition.

15. A method as set forth in claim 11 wherein said step of enclosing at least the computer and radio at each of the gas monitor stations with an explosion-proof housing includes enclosing the computer and radio at each of the gas monitor stations with an explosion-proof housing which is operable between an open condition in which an interior of the explosion-proof housing is in fluid communication with atmosphere adjacent to the gas monitor station and a closed condition in which the interior of the explosion-proof housing is sealed against entry of gas from atmosphere adjacent to the gas monitor station, said step of entering data relating to the selected gas is performed with the explosion-proof housing in the closed condition.

16. A method as set forth in claim 15 wherein said step of entering data relating to the selected gas includes transmitting data from a radio at the master station to the radio at each of the gas monitor stations.

17. A method as set forth in claim 11 further including the steps of transmitting a computer program change from the master station to the radio in at least one of the gas monitor stations and changing a program in the computer in at least one of the monitor stations in accordance with the computer program change transmitted by radio from the master station.

18. A method as set forth in claim 11 further including the step of determining when the concentration of the selected gas in the atmosphere adjacent to anyone of the gas monitor stations has changed by more than a predetermined amount and transmitting a radio signal from the one gas monitor station to the master station in response to a determination that the concentration of the selected gas in the atmosphere adjacent to the one gas monitor station has changed by more than the predetermined amount.

19. A method as set forth in claim 11 further including the steps of determining at each of the gas monitor stations the length of time which has elapsed since transmission of a radio signal and transmitting a radio signal from anyone of the gas monitor stations to the master station upon determining that a predetermined length of time has elapsed since transmission of a radio signal.

20. A method as set forth in claim 19 further including the step of determining at the master station when the length of time which has elapsed since transmission of a radio signal from anyone of the gas monitor stations has exceeded a length of time which is longer than the predetermined length of time and providing an alarm signal at the master station in response to a determination that the length of time which has elapsed since transmission of a radio signal from anyone of the gas monitor stations has exceeded the length of time which is longer than the predetermined length of time.

21. A method as set forth in claim 11 further including the steps of transmitting a predetermined input voltage to a sensor at a gas monitor station, transmitting from the sensor at the gas monitor station an output voltage which is a function of the input voltage and the condition of the sensor, and determining if the sensor at the gas monitor station should be replaced as a function of the output voltage from the sensor.

22. A method of monitoring for a selected gas in an environment which may contain ignitable concentrations of flammable gas, said method comprises installing a gas monitor assembly in the environment which may contain ignitable concentrations of flammable gas, said step of installing a gas monitor assembly includes preventing ignition of any flammable gases around the gas monitor assembly by a spark within a housing for at least a portion of the gas monitor assembly by sealing the housing against entry of gas from around the gas monitor assembly, entering data into the gas monitor assembly by transmitting data from a location outside the housing to the portion of the gas monitor assembly in the housing, said step of entering data into the portion of the gas monitor assembly in the housing includes entering data relating to a predetermined concentration of a selected gas, thereafter, sensing the atmosphere outside the housing, initiating transmission with a radio in the housing when the sensed concentration of the selected gas in the atmosphere adjacent to the gas monitor assembly is at least as great as the predetermined concentration of the selected gas, and transmitting data corresponding to the sensed concentration of the selected gas from the radio in the housing to a master station while maintaining the housing in a sealed condition to prevent ignition of flammable gas around the gas monitor assembly by a spark within the housing during transmission of data from the radio in the housing.

23. A method as set forth in claim 22 wherein said step of transmitting data from a location outside the housing to the portion of the gas monitor assembly in the housing includes transmitting a radio signal from a master station spaced from the gas monitor assembly to the radio within the housing while maintaining the housing in a sealed condition.

24. A method as set forth in claim 22 wherein said step of transmitting data from a location outside the housing to the portion of the gas monitor assembly in the housing includes transmitting data from a data input device to control apparatus disposed within the housing.

25. A method as set forth in claim 24 wherein said step of transmitting data from a data input device to control apparatus in the housing includes opening an enclosure which encloses the data input device, and transmitting data from the data input device to the control apparatus in the housing.

26. A method as set forth in claim 22 wherein the housing includes a base and a cover which is secured to the base by a plurality of fasteners, said step of entering data into the portion of the gas monitor assembly in the housing includes releasing the plurality of fasteners, moving the cover from a closed condition to an open condition, and manually actuating switches enclosed by the housing when the cover is in the closed condition.

27. A method as set forth in claim 22 wherein the housing includes a base and a cover which is secured to the base, said step of entering data into the portion of the gas monitor assembly in the housing is performed with the cover in a closed condition, said step of entering data into the portion of the gas monitor assembly in the housing includes transmitting the data from a location outside of the housing.

28. A method as set forth in claim 22 wherein said step of installing a gas monitor assembly includes providing a plurality of sensors which are capable of sensing a plurality of different gases, said step of entering data includes entering data relating to a predetermined concentration of each gas of the plurality of different gases, said step of transmitting data includes transmitting data corresponding to the sensed concentration of each of the gases of the plurality of gases.

29. A method of monitoring for a selected gas from a potential source of the selected gas, said method comprising the steps of providing a plurality of gas monitor stations at locations spaced from the potential source of the selected gas and from a master station, said step of providing a plurality of gas monitor stations includes providing a programmable computer connected with a radio and a sensor at each of the gas monitor stations, transmitting a computer program change from a radio in the master station to the radio in at least a first gas monitor station, changing a program in the computer in at least the first gas monitor station in accordance with the computer program change transmitted by radio from the master station, transmitting data relating to the selected gas from the radio in the master station to the radio in at least the first gas monitor station, storing the data relating to the selected gas transmitted to the radio in the first gas monitor station in the computer in the first gas monitor station, sensing atmosphere adjacent to the first gas monitor station, operating the computer in the first gas monitor station in accordance with the program change transmitted from the master station, transmitting a radio signal from the first gas monitor station to the master station when operation of the computer in the first gas monitor station indicates that a sensed concentration of the selected gas in the atmosphere adjacent to the first gas monitor station is in accordance with a function of the data stored in the computer in the first gas monitor station.

30. A method as set forth in claim 29, wherein said step of providing a plurality of gas monitor stations includes enclosing the computer and radio at each of the gas monitor stations in a housing which is sealed against entry of gas from the atmosphere around the gas monitor station.

31. A method as set forth in claim 29 further including the steps of determining at each of the gas monitor stations the length of time which has elapsed since transmission of a radio signal, and transmitting a radio signal from anyone of the gas monitor stations to the master station upon determining that a predetermined period of time has elapsed since transmission of a radio signal from the one gas monitor station.

32. A method as set forth in claim 29 wherein said step of transmitting data relating to the selected gas from the radio in the master station to the radio in the first gas monitor station includes transmitting data relating to an average permissible magnitude of concentration of the selected gas over a predetermined period of time at the first gas monitor station, and transmitting a radio signal from the first gas monitor station to the master station in response to sensing of an average concentration of the selected gas greater than the permissible magnitude.

33. A method as set forth in claim 29 further including the step of eliminating the effect of transient variations in the concentration of the selected gas in the atmosphere adjacent to the first gas monitor station by averaging the sensed magnitude of the selected gas over a period of time of thirty seconds or less.

34. A method as set forth in claim 29 wherein the radio at the first gas monitor station utilizes electrical energy at a first rate when the radio at the first gas monitor station is in a transmit mode and is transmitting to the master station and utilizes electrical energy at a second rate which is less than the first rate when the radio at the first gas monitor station is in a standby mode, said method further includes maintaining the radio at the first gas monitor station in the standby mode except when the radio at the first gas monitor station is transmitting.

35. A method as set forth in claim 29 wherein said step of transmitting data relating to the selected gas from the radio in the master station to the radio in the first gas monitor station includes transmitting data relating to a moving average gas concentration over a predetermined length of time, said method further includes determining when the moving average of sensed concentration over a predetermined length of time of the selected gas in the atmosphere adjacent to the first gas monitor station exceeds a predetermined magnitude, and transmitting a radio signal from the radio at the first gas monitor station to the master station in response to a determination that the moving average concentration of the selected gas over the predetermined length of time exceeds the predetermined magnitude.

36. A method as set forth in claim 29 further including the steps of transmitting a predetermined input voltage to a sensor at each of the gas monitor stations, transmitting an output voltage from the sensor at each of the gas monitor stations, and determining if the sensor at anyone of the gas monitor stations should be replaced as a function of the magnitude of the output voltage.

37. A method of monitoring a selected operating condition, said method comprising the steps of providing a plurality of monitor stations at spaced apart locations in an environment which may contain an ignitable concentration of flammable gas, said step of providing a plurality of monitor stations includes providing a programmable computer connected with a radio and a sensor at each of the monitor stations and preventing ignition of any flammable gas around the gas monitor stations by a spark within a housing for the computer and radio at anyone of the monitor stations by sealing the housings against entry of gas from around the gas monitor stations, transmitting a computer program change from a master station radio to the radio in at least one of the monitor stations, changing a program in the computer in at least one of the monitor stations in accordance with the computer program change transmitted by radio from the master station, sensing conditions with the sensors at the monitor stations, operating a computer at each of the monitor stations in accordance with a program in the computer at each of the monitor stations, and transmitting a radio signal from at least one of the monitor stations to the master station in response to sensing of a predetermined condition.

38. A method as set forth in claim 37 wherein said step of sensing conditions at each of the monitor stations includes sensing atmosphere adjacent to the monitor stations while the housings for the computers and radios at the gas monitor stations remain sealed, said step of transmitting a radio signal from at least one of the monitor stations to the master station in response to sensing of a predetermined condition includes transmitting a radio signal in response to the sensing of a variation in concentration of a selected gas in the atmosphere.

39. A method as set forth in claim 37 further including the step of transmitting a change in magnitude of data stored in a computer from the master station to a selected one of the monitor stations, changing the magnitude of the data stored in the computer at the selected one of the monitor stations without changing the program in the computer at the selected one of the monitor stations, transmitting a radio signal from the selected one of the monitor stations to the master station in response to sensing of a condition corresponding to the changed magnitude of the data stored in the computer at the selected one of the monitor stations.

40. A method as set forth in claim 37 wherein said step of operating a computer at each of the monitor stations includes performing a step-by-step procedure with the computer at each of the monitor stations in accordance with a program in each of the computers, said step of transmitting a radio signal from at least one of the monitor stations to the master station in response to sensing of a predetermined condition includes transmitting a radio signal from the one monitor station to the master station when performance of the step-by-step procedure results in the sensed condition corresponding to a predetermined function of data stored in the computer at the one monitor station.

41. A method as set forth in claim 37 further including the step of entering data relating to a predetermined magnitude of concentration of a the data from the radio at the master station to each of the radios at the monitor stations and storing the data received by each of the radios at each of the monitor stations in the computers at each of the monitor stations while the housings for the computers and radios at the gas monitor stations remain sealed.

42. A method as set forth in claim 37 wherein said step of sensing conditions at each of the monitor stations includes sensing atmosphere adjacent to each of the monitor stations, said step of operating a computer at each of the monitor stations includes determining when a sensed concentration of the selected gas is a predetermined function of the predetermined concentration of the selected gas, said step of transmitting a radio signal from at least one of the monitor stations to the master station is performed in response to the computer at the one monitor station determining that the sensed concentration of the selected gas is the predetermined function of the predetermined concentration of the selected gas.

43. A method of monitoring a selected operating condition, said method comprising the steps of providing a plurality of monitor stations at spaced apart locations, said step of providing a plurality of monitor stations includes providing a programmable computer connected with a radio and a sensor at each of the monitor stations, transmitting a computer program change from a master station radio to the radio in at least one of the monitor stations, changing a program in the computer in at least one of the monitor stations in accordance with the computer program change transmitted by radio from the master station, entering data relating to a predetermined magnitude of concentration of a selected gas into computers at each of the monitor stations by transmitting the data from the radio at the master station to each of the radios at the monitor stations and storing the data received by each of the radios at each of the monitor stations in the computers at each of the monitor stations, sensing conditions with the sensors at the monitor stations, operating a computer at each of the monitor stations in accordance with a program in the computer at each of the monitor stations, and transmitting a radio signal from at least one of the monitor stations to the master station in response to sensing of a predetermined condition.

44. A method as set forth in claim 43 wherein said step of sensing conditions at each of the monitor stations includes sensing atmosphere adjacent to at least one of the monitor stations, said step of transmitting a radio signal from at least one of the monitor stations to the master station in response to sensing of a predetermined condition includes transmitting a radio signal in response to the sensing of a variation in concentration of the selected gas in the atmosphere.

45. A method as set forth in claim 43 wherein said step of sensing conditions at each of the monitor stations includes sensing fluid flow with a sensor at one of the monitor stations, said step of transmitting a radio signal from at least one of the monitor stations to the master station in response to sensing of a predetermined condition includes transmitting a radio signal in response to the sensing of a variation in the fluid flow.

46. A method as set forth in claim 45 wherein said step of sensing fluid flow with a sensor includes sensing fluid flow in a conduit.

47. A method as set forth in claim 43 wherein said step of sensing conditions at each of the monitor stations includes sensing temperature with a sensor at one of the monitor stations, said step of transmitting a radio signal from at least one of the monitor stations to the master station in response to sensing of a predetermined condition includes transmitting a radio signal in response to the sensing of a variation in temperature.

48. A method as set forth in claim 43 wherein said step of sensing conditions at each of the monitor stations includes sensing force with a sensor at one of the monitor stations, said step of transmitting a radio signal from at least one of the monitor stations to the master station in response to sensing of a predetermined condition includes transmitting a radio signal in response to the sensing of a variation in force.

49. A method as set forth in claim 43 further including the step of transmitting a change in magnitude of data stored in a computer from the master station to a selected one of the monitor stations, changing the magnitude of the data stored in the computer at the selected one of the monitor stations without changing the program in the computer at the selected one of the monitor stations, transmitting a radio signal from the selected one of the monitor stations to the master station in response to sensing of a condition corresponding to the changed magnitude of the data stored in the computer at the selected one of the monitor stations.

50. A method as set forth in claim 43 wherein said step of operating a computer at each of the monitor stations includes performing a step-by-step procedure with the computer at each of the monitor stations in accordance with a program in each of the computers, said step of transmitting a radio signal from at least one of the monitor stations to the master station in response to sensing of a predetermined condition includes transmitting a radio signal from the one monitor station to the master station when performance of the step-by-step procedure results in the sensed condition corresponding to a predetermined function of data stored in the computer at the one monitor station.

51. A method as set forth in claim 43 wherein providing a plurality of monitor stations at spaced apart locations includes providing a plurality of gas monitor stations in an environment which may contain ignitable concentrations of flammable gas, said step of providing a plurality of gas monitor stations includes preventing ignition of any flammable gas around the gas monitor stations by a spark within a housing for the computer and radio by sealing the housing against entry of gas from around gas monitor station.

52. A method as set forth in claim 43 wherein said step of sensing conditions at each of the monitor stations includes sensing atmosphere adjacent to each of the monitor stations, said step of operating a computer at each of the monitor stations includes determining when a sensed concentration of the selected gas is a predetermined function of the predetermined concentration of the selected gas, said step of transmitting a radio signal from at least one of the monitor stations to the master station is performed in response to the computer at the one monitor station determining that the sensed concentration of the selected gas is the predetermined function of the predetermined concentration of the selected gas.

53. A method of monitoring a selected operating condition, said method comprising the steps of providing a plurality of monitor stations at locations which are spaced from a master station, said step of providing a plurality of monitor stations includes providing a computer connected with a radio and a sensor at each of the monitor stations, transmitting data from a radio at the master station to each of the monitor stations, storing the data transmitted to the radios at each of the monitor stations in the computers at each of the monitor stations, sensing conditions with the sensors at each of the monitor stations, and transmitting a radio signal from the radio at anyone of the monitor stations to the radio at the master station in response to sensing of a condition which is a function of the data stored in the computer at the one monitor station, said step of providing a plurality of monitor stations includes providing a plurality of gas monitor stations in an environment which may contain ignitable concentrations of flammable gas, said step of providing a plurality of gas monitor stations includes preventing ignition of any flammable gas around the gas monitor stations by a spark within a housing for the computer and radio by sealing the housing against entry of gas from around gas monitor station.

54. A method as set forth in claim 53 further including the steps of determining at each of the gas monitor stations the length of time which has elapsed since transmission of a radio signal, and transmitting a radio signal from anyone of the gas monitor stations to the master station upon determining that a predetermined period of time has elapsed since transmission of a radio signal.

55. A method as set forth in claim 53 wherein said step of transmitting data from a radio at the master station to each of the monitor stations includes transmitting data relating to an average permissible magnitude of concentration of the flammable gas over a predetermined period of time, and transmitting a radio signal from anyone of the gas monitor stations to the master station in response to sensing of an average concentration of the flammable gas greater than the permissible magnitude.

56. A method as set forth in claim 53 further including the step of eliminating the effect of transient variations in the concentration of the flammable gas in the atmosphere adjacent to the gas monitor stations by averaging the sensed magnitude of the flammable gas over a period of time of thirty seconds or less.

57. A method as set forth in claim 53 wherein the radio at each gas monitor station utilizes electrical energy at a first rate when the radio is in a transmit mode and is transmitting to the master station and utilizes electrical energy at a second rate which is less than the first rate when the radio is in a standby mode, said method further includes maintaining the radio at each of the gas monitor stations in the standby mode except when the radio is transmitting.

58. A method as set forth in claim 53 wherein said step of transmitting data from a radio at the master station to each of the gas monitor stations includes transmitting data relating to a moving average gas concentration over a predetermined length of time, said method further includes determining when the moving average of sensed concentration over a predetermined length of time of the flammable gas in the atmosphere adjacent to one of the monitor stations exceeds a predetermined magnitude, and transmitting a radio signal to the master station in response to a determination that the moving average concentration of the flammable gas over the predetermined length of time exceeds the predetermined magnitude.

59. A method as set forth in claim 53 further including the steps of transmitting a predetermined input voltage to the sensor at each of the gas monitor stations, transmitting an output voltage from the sensor at each of the gas monitor stations, determining if the sensor at anyone of the gas monitor stations should be replaced as a function of the magnitude of the output voltage, and transmitting a radio signal from the radio at a gas monitor station to the radio at the master station in response to a determination that a sensor should be replaced.

60. A method as set forth in claim 53 further including the steps of transmitting a computer program change from the radio at the master station to the radio in at least one of the gas monitor stations, changing a program in at least one of the computers in at least one of the gas monitor stations in accordance with the computer program change transmitted by radio from the master station.

61. A method as set forth in claim 60 further including the step of transmitting a change in magnitude of a set point in a computer program from the radio in the master station to the radio in at least one of the gas monitor stations, and changing the magnitude of the set point in the program in the computer in at least one of the gas monitor stations without changing the program in the computer.

62. A method of monitoring for a selected gas, said method comprising the steps of positioning a plurality of portable gas monitor stations at a plurality of locations spaced from a master station, said step of positioning a plurality of portable gas monitor stations includes positioning portable gas monitor stations having a global positioning system receiver, a gas sensor, and a radio at each of the locations, processing satellite signals received by the global positioning system receivers at each of the gas monitor stations to determine the location of each of the gas monitor stations, transmitting a signal indicative of a position of each portable gas monitor station from a radio at each portable gas monitor station to the master station, transmitting data relating to the selected gas from a radio at the master station to the radios at each of the portable gas monitor stations, storing the data transmitted from the master station and relating to the selected gas in the computers at each of the portable gas monitor stations, sensing atmosphere adjacent to each of the portable gas monitor stations, and transmitting a signal from the radio at anyone of the portable gas monitor stations to the radio at the master station in response to sensing of a predetermined concentration of the selected gas.

63. A method as set forth in claim 62 wherein said step of positioning a plurality of portable gas monitor stations includes positioning a portable gas monitor station having an explosion-proof housing which is sealed against entry of gas from the atmosphere at each of the locations.

64. A method as set forth in claim 62 further including the step of changing a program in the computer in at least one of the portable gas monitor stations in accordance with a computer program change transmitted by radio from the master station.

65. A method as set forth in claim 62 further including the steps of determining at each of the portable gas monitor stations the length of time which has elapsed since transmission of a radio signal, and transmitting a radio signal from anyone of the portable gas monitor stations to the master station upon determining that a predetermined period of time has elapsed since transmission of a radio signal.

66. A method as set forth in claim 62 wherein said step of transmitting data from the master station to each of the portable gas monitor stations includes transmitting data relating to an average permissible magnitude of concentration of the selected gas over a predetermined period of time, and transmitting a radio signal from any one of the portable gas monitor stations to the master station in response to sensing of an average concentration of the selected gas greater than the permissible magnitude.

67. A method as set forth in claim 62 further including the step of eliminating the effect of transient variations in the concentration of the selected gas in the atmosphere adjacent to the portable gas monitor stations by averaging the sensed magnitude of the selected gas over a period of time of thirty seconds or less.

68. A method as set forth in claim 62 wherein a radio at each portable gas monitor station utilizes electrical energy at a first rate when the radio is in a transmit mode and is transmitting to the master station and utilizes electrical energy at a second rate which is less than the first rate when the radio is in a standby mode, said method further includes maintaining the radio at each of the portable gas monitor stations in the standby mode except when the radio is transmitting.

69. A method as set forth in claim 62 wherein said step of transmitting data from the master station to each of the portable gas monitor stations includes transmitting data relating to a moving average gas concentration over a predetermined length of time, said method further includes determining when the moving average of sensed concentration over a predetermined length of time of the selected gas in the atmosphere adjacent to one of the portable gas monitor stations exceeds a predetermined magnitude, and transmitting a radio signal to the master station in response to a determination that the moving average concentration of the selected gas over the predetermined length of time exceeds the predetermined magnitude.

70. A method as set forth in claim 62 further including the steps of transmitting a predetermined input voltage to a sensor at each of the portable gas monitor stations, transmitting an output voltage from the sensor at each of the portable gas monitor stations, determining if the sensor at any one of the portable gas monitor stations should be replaced as a function of the magnitude of the output voltage, and transmitting a radio signal from the radio at a portable gas monitor station to the radio at the master station in response to a determination that a sensor should be replaced.

71. A method as set forth in claim 62 further including the steps of transmitting a computer program change from the master station radio to the radio in at least one of the portable gas monitor stations, and changing a program in at least one of the computers in at least one of the portable gas monitor stations in accordance with the computer program change transmitted by radio from the master station.

72. A method as set forth in claim 71 further including the steps of transmitting a change in magnitude of a set point in a computer program from the radio in the master station to the radio in at least one of the portable gas monitor stations, and changing the magnitude of the set point in the program in the computer in at least one of the portable gas monitor stations without changing the program in the computer.

73. A method as set forth in claim 62 wherein said step of providing a plurality of portable gas monitor stations includes enclosing the computer and radio at each of the portable gas monitor stations in an explosion-proof housing which is sealed against entry of gas from the atmosphere around the portable gas monitor station.

74. A method of monitoring for a selected gas, said method comprising the steps of positioning a plurality of portable gas monitor stations at a plurality of locations spaced from a master station, said step of positioning a plurality of portable gas monitor stations includes positioning portable gas monitor stations having a global positioning system receiver, a gas sensor, and a radio at each of the locations, processing satellite signals received by the global positioning system receivers at each of the gas monitor stations to determine the location of each of the gas monitor stations, said step of positioning a plurality of portable gas monitor stations includes positioning a portable gas monitor station having an explosion-proof housing which is sealed against entry of gas from the atmosphere at each of the locations, transmitting a signal indicative of a position of each portable gas monitor station from a radio at each portable gas monitor station to the master station, sensing atmosphere adjacent to each of the portable gas monitor stations, and transmitting a signal from the radio at anyone of the portable gas monitor stations to the radio at the master station in response to sensing of a predetermined concentration of the selected gas.

75. A method as set forth in claim 74 further including the step of changing a program in the computer in at least one of the portable gas monitor stations in accordance with a computer program change transmitted by radio from the master station.

76. A method of monitoring for a selected gas from a potential source of the selected gas, said method comprising the steps of providing a plurality of gas monitor stations at locations spaced from the potential source of the selected gas and from a master station, said step of providing a plurality of gas monitor stations includes providing a housing which encloses a computer and a radio and which is connected with a sensor at each of the gas monitor stations, said step of providing a housing includes providing a housing which is sealed against entry of gas from the atmosphere around the gas monitor station, transmitting data relating to the selected gas to at least one of the computers at one of the gas monitor stations, said step of transmitting data relating to the selected gas is performed while the housing enclosing the computer to which the data is being transmitted is sealed against entry of gas from the atmosphere, sensing the atmosphere adjacent to the gas monitor stations while the housings at the gas monitor stations are sealed, and transmitting a signal from the radio at the one gas monitor station to a radio at a master station in response to sensing of a concentration of the selected gas which is a function of the data transmitted to the computer at the one gas monitor station.

77. A method as set forth in claim 76 further including the steps of determining at each of the gas monitor stations the length of time which has elapsed since transmission of a radio signal, and transmitting a radio signal from any one of the gas monitor stations to the master station upon determining that a predetermined period of time has elapsed since transmission of a radio signal.

78. A method as set forth in claim 76 wherein said step of transmitting data relating to the selected gas to the computer at the one gas monitor station includes transmitting data relating to an average permissible magnitude of concentration of the selected gas over a predetermined period of time, and transmitting a radio signal from the one gas monitor station to the master station in response to sensing of an average concentration of the selected gas greater than the permissible magnitude.

79. A method as set forth in claim 76 wherein said step of transmitting data relating to the selected gas to the computer at the one gas monitor station is performed by operating the radio at the master station.

80. A method as set forth in claim 76 wherein said step of transmitting data relating to the selected gas to the computer at one of the gas monitor stations includes opening a secondary housing which is connected with the housing which encloses the computer and radio at the one gas monitor station, connecting a data entry device with a terminal in the secondary housing, and transmitting data from the data entry device to the terminal in the secondary housing.

81. A method as set forth in claim 76 further including the step of eliminating the effect of transient variations in the concentration of the selected gas in the atmosphere adjacent to the gas monitor stations by averaging the sensed magnitude of the selected gas over a period of time of thirty seconds or less.

82. A method as set forth in claim 76 wherein a radio at each gas monitor station utilizes electrical energy at a first rate when the radio is in a transmit mode and is transmitting to the master station and utilizes electrical energy at a second rate which is less than the first rate when the radio is in a standby mode, said method further includes maintaining the radio at each of the gas monitor stations in the standby mode except when the radio is transmitting.

83. A method as set forth in claim 76 wherein said step of transmitting data to the computer at the one of the gas monitor stations includes transmitting data relating to a moving average gas concentration over a predetermined length of time, said method further includes determining when the moving average of sensed concentration over a predetermined length of time of the selected gas in the atmosphere adjacent to the one of the gas monitor stations exceeds a predetermined magnitude, and transmitting to the master station in response to a determination that the moving average concentration of the selected gas over the predetermined length of time exceeds the predetermined magnitude.

84. A method as set forth in claim 83 wherein said step of transmitting data to the computer at the one gas monitor station includes transmitting data from the master station to the computer at the one gas monitor station.

85. A method as set forth in claim 76 wherein said step of transmitting data to the computer at the one gas monitor station includes transmitting data from a data entry device.

86. A method as set forth in claim 76 further including the steps of transmitting a predetermined input voltage to a sensor at each of the gas monitor stations, transmitting an output voltage from the sensor at each of the gas monitor stations, determining if the sensor at any one of the gas monitor stations should be replaced as a function of the magnitude of the output voltage, and transmitting a radio signal from the radio at a gas monitor station to the radio at the master station in response to a determination that a sensor should be replaced.

87. A method as set forth in claim 76 further including the steps of transmitting a computer program change from the radio at the master station to the radio in at least one of the gas monitor stations, and changing a program in at least one of the computers in at least one of the gas monitor stations in accordance with the computer program change transmitted by radio from the master station.

88. A method as set forth in claim 76 further including the steps of transmitting a change in magnitude of a set point in a computer program from the radio in the master station to the radio in at least one of the gas monitor stations, and changing the magnitude of the set point in the program in the computer in at least one of the gas monitor stations without changing the program in the computer.

89. A method of monitoring for a selected gas from a potential source of the selected gas, said method comprising the steps of providing a gas monitor station having a housing which encloses a radio and a computer, opening the housing by rotating a circular cover in a first direction relative to a base portion of the housing, said step of opening the housing by rotating the cover includes rotating the cover about a central axis of the cover, performing at least one action while the housing is open, closing the housing after performing the at least one action, said step of closing the housing includes rotating the cover in a second direction opposite to the first direction to form a gas tight seal between the cover and the base portion of the housing, transmitting data relating to the selected gas to the computer in the housing with the housing closed and with a gas tight seal between the cover and the base portion of the housing, sensing the atmosphere adjacent to the gas monitor station with a gas sensor which is connected with the housing while the housing is closed and while there is a gas a gas tight seal between the cover and base portion of the housing, said step of sensing the atmosphere with the gas sensor is at least partially performed after performing said step of transmitting data relating to the selected gas to the computer in the housing, and transmitting a signal from the radio in the housing to a receiving location after sensing the selected gas, said step of transmitting a signal from the radio in the housing is performed with the housing closed and with a gas tight seal between the cover and the base portion of the housing.

90. A method as set forth in claim 89 wherein said step of transmitting data relating to the selected gas to the computer in the housing with the housing closed includes transmitting data to the radio in the housing and transmitting data from the radio to the computer in the housing, said step of transmitting a signal from the radio in the housing to the receiving location after sensing of the selected gas is performed in response to sensing of a concentration of the selected gas which is a function of the data transmitted to the computer in the housing.

91. A method as set forth in claim 89 further including the steps of determining the length of time which has elapsed since transmission of a signal from the radio in the housing, and transmitting a radio signal upon determining that a predetermined period of time has elapsed since transmission of a radio signal.

92. A method as set forth in claim 89 wherein said step of transmitting data relating to the selected gas to the computer in the housing includes transmitting data relating to an average permissible magnitude of concentration of the selected gas over a predetermined period of time, said step of transmitting a signal from the radio in the housing being performed in response to sensing of an average concentration of the selected gas greater than the permissible magnitude.

93. A method as set forth in claim 89 further including the step of eliminating the effect of transient variations in the concentration of the selected gas in the atmosphere adjacent to the gas monitor station by averaging the sensed magnitude of the selected gas over a period of time of thirty seconds or less.

94. A method as set forth in claim 89 wherein the radio at the gas monitor station utilizes electrical energy at a first rate when the radio is in a transmit mode and is transmitting and utilizes electrical energy at a second rate which is less than the first rate when the radio is in a standby mode, said method further includes maintaining the radio in the standby mode except when the radio is transmitting.

95. A method as set forth in claim 89 wherein said step of transmitting data relating to the selected gas to the computer in the housing includes transmitting data relating to a moving average gas concentration over a predetermined length of time, said method further includes determining when the moving average of sensed concentration over a predetermined length of time of the selected gas in the atmosphere adjacent to the gas monitor station exceeds a predetermined magnitude, and transmitting a radio signal to the receiving location in response to a determination that the moving average concentration of the selected gas over the predetermined length of time exceeds the predetermined magnitude.

96. A method as set forth in claim 89 further including the steps of transmitting a predetermined input voltage to a sensor at the gas monitor station, transmitting an output voltage from the sensor at the gas monitor station, determining if the sensor at the gas monitor station should be replaced as a function of the magnitude of the output voltage, and transmitting a radio signal from the radio at the gas monitor station in response to a determination that a sensor should be replaced.

97. A method as set forth in claim 89 further including the steps of transmitting a computer program change to the radio in the gas monitor station, and changing a program in the computer in the gas monitor station in accordance with the computer program change transmitted to the radio in the gas monitor station.

98. A method as set forth in claim 89 further including the steps of transmitting a change in magnitude of a set point in a computer program to the radio in the gas monitor station, and changing the magnitude of the set point in a program in the computer in the gas monitor station without changing the program in the computer.

99. A method as set forth in claim 89 wherein said step of transmitting data relating to the selected gas to the computer in the housing with the housing closed includes operating a radio at the receiving location.

100. A method as set forth in claim 89 wherein said step of sensing the atmosphere adjacent to the gas monitor station is continued during and after performance of said step of transmitting a signal from the radio in the housing.

101. A method of monitoring for a selected gas from a potential source of the selected gas, said method comprising the steps of providing a gas monitor station having a housing which encloses a radio and a computer, said housing having a base, a first cover, and a second cover which is smaller than the first cover, moving the first cover between a closed condition in which said first cover is sealed against entry of gas from an environment around the gas monitor station and an open condition, performing at least one action while the first cover is in the open condition, moving the second cover between a closed condition in which the second cover is sealed against entry of gas from the environment around the gas monitor station and an open condition, performing at least one action while the second cover is in the open condition, transmitting data relating to the selected gas to the computer in the housing while the first and second covers are in their closed conditions and with the housing sealed against entry of gas from the environment around the gas monitor station, sensing the atmosphere adjacent to the gas monitor station while the first and second covers are in their closed conditions sealed against entry of gas from the environment around the gas monitor station, said step of sensing the atmosphere adjacent to the gas monitor station is at least partially performed after performing said step of transmitting data relating to the selected gas to the computer in the housing, and transmitting a signal from the radio in the housing to a receiving location after sensing the selected gas, said step of transmitting a signal from the radio in the housing is performed while the first and second covers are in their closed conditions sealed against entry of gas from the environment around the gas monitor station.

102. A method as set forth in claim 101 wherein said step of transmitting data relating to the selected gas to the computer in the housing with the first and second covers in their closed conditions includes transmitting data to the radio in the housing and transmitting data from the radio to the computer in the housing, said step of transmitting a signal from the radio in the housing to the receiving location after sensing of the selected gas is performed in response to sensing of a concentration of the selected gas which is a function of the data transmitted to the computer in the housing.

103. A method as set forth in claim 101 further including the steps of determining the length of time which has elapsed since transmission of a signal from the radio in the housing, and transmitting a radio signal upon determining that a predetermined period of time has elapsed since transmission of a radio signal.

104. A method as set forth in claim 101 wherein said step of transmitting data relating to the selected gas to the computer in the housing includes transmitting data relating to an average permissible magnitude of concentration of the selected gas over a predetermined period of time, said step of transmitting a signal from the radio in the housing being performed in response to sensing of an average concentration of the selected gas greater than the permissible magnitude.

105. A method as set forth in claim 101 further including the step of eliminating the effect of transient variations in the concentration of the selected gas in the atmosphere adjacent to the gas monitor station by averaging the sensed magnitude of the selected gas over a period of time of thirty seconds or less.

106. A method as set forth in claim 101 wherein the radio at the gas monitor station utilizes electrical energy at a first rate when the radio is in a transmit mode and is transmitting and utilizes electrical energy at a second rate which is less than the first rate when the radio is in a standby mode, said method further includes maintaining the radio in the standby mode except when the radio is transmitting.

107. A method as set forth in claim 101 wherein said step of transmitting data relating to the selected gas to the computer in the housing includes transmitting data relating to a moving average gas concentration over a predetermined length of time, said method further includes determining when the moving average of sensed concentration over a predetermined length of time of the selected gas in the atmosphere adjacent to the gas monitor station exceeds a predetermined magnitude, and transmitting a radio signal to the receiving location in response to a determination that the moving average concentration of the selected gas over the predetermined length of time exceeds the predetermined magnitude.

108. A method as set forth in claim 101 further including the steps of transmitting a predetermined input voltage to a sensor at the gas monitor station, transmitting an output voltage from the sensor at the gas monitor station, determining if the sensor at the gas monitor station should be replaced as a function of the magnitude of the output voltage, and transmitting a radio signal from the radio at the gas monitor station in response to a determination that a sensor should be replaced.

109. A method as set forth in claim 101 further including the steps of transmitting a computer program change to the radio in the gas monitor station, and changing a program in the computer in the gas monitor station in accordance with the computer program change transmitted to the radio in the gas monitor station.

110. A method as set forth in claim 101 further including the steps of transmitting a change in magnitude of a set point in a computer program to the radio in the gas monitor station, and changing the magnitude of the set point in a program in the computer in the gas monitor station without changing the program in the computer.

111. A method as set forth in claim 101 wherein said step of transmitting data relating to the selected gas to the computer in the housing while the first and second covers are in their closed conditions includes operating a radio at the receiving location.

112. A method as set forth in claim 101 wherein said step of sensing the atmosphere adjacent to the gas monitor station is continued during and after performance of said step of transmitting a signal from the radio in the housing.

113. A method as set forth in claim 101 wherein said step of moving the second cover between the closed condition and the open condition includes rotating the second cover about a central axis of the second cover.

114. A method as set forth in claim 101 wherein the second cover is spaced from the first cover, said step of moving the first cover between the closed condition in which the first cover is sealed and the open condition includes moving the first cover between the closed condition in which the first cover is disposed in a sealing relationship with a first portion of a base of the housing and the open condition in which the first cover is spaced from the first portion of the base of the housing, said step of moving the second cover between the closed condition in which the second cover is sealed and the open condition includes moving the second cover between the closed condition in which the second cover is disposed in a sealing relationship with a second portion of the base of the housing which is spaced from the first portion of the base of the housing and the open condition in which the second cover is spaced from the second portion of the base of the housing.

* * * * *